United States Patent
Fish et al.

(10) Patent No.: US 11,013,852 B2
(45) Date of Patent: May 25, 2021

(54) MEDICAL INFUSION PUMP FOR SEQUENTIALLY INJECTING SOLUTIONS FROM MULTIPLE SYRINGES

(71) Applicants: Tyler G. Fish, Lehi, UT (US); Elisabeth M. Fish, Lehi, UT (US); Aaron Schellenberg, Rexburg, ID (US)

(72) Inventors: Tyler G. Fish, Lehi, UT (US); Elisabeth M. Fish, Lehi, UT (US); Aaron Schellenberg, Rexburg, ID (US)

(73) Assignees: Tyler G. Fish, Lehi, UT (US); Elisabeth M. Fish, Lehi, UT (US)

( * ) Notice: Subject to any disclaimer, the term of this patent is extended or adjusted under 35 U.S.C. 154(b) by 925 days.

(21) Appl. No.: 15/614,411

(22) Filed: Jun. 5, 2017

(65) Prior Publication Data
US 2017/0266367 A1    Sep. 21, 2017

Related U.S. Application Data

(62) Division of application No. 14/856,091, filed on Sep. 16, 2015, now Pat. No. 9,981,082.

(51) Int. Cl.
| | |
|---|---|
| *A61M 5/14* | (2006.01) |
| *A61M 5/145* | (2006.01) |
| *A61M 5/168* | (2006.01) |
| A61M 5/178 | (2006.01) |
| A61M 5/19 | (2006.01) |

(52) U.S. Cl.
CPC ........ *A61M 5/1408* (2013.01); *A61M 5/1407* (2013.01); *A61M 5/1452* (2013.01); *A61M 5/16881* (2013.01); *A61M 5/19* (2013.01); *A61M 2005/14506* (2013.01); *A61M 2005/1787* (2013.01)

(58) Field of Classification Search
CPC .............. A61M 5/1456; A61M 5/1452; A61M 5/1458; A61M 5/1408; A61M 2005/14506; A61M 5/1454; A61M 5/315; A61M 5/142; A61M 5/145; A61M 2005/14533; A61M 5/14546; A61M 2005/14553; A61M 5/14566; A61M 2005/14573; A61M 5/1407; A61M 5/14; A61M 5/2046; A61M 5/155; A61M 5/2033; A61M 5/19; A61M 2005/1787
See application file for complete search history.

(56) References Cited

U.S. PATENT DOCUMENTS

| | | | | |
|---|---|---|---|---|
| 2,309,502 | A * | 1/1943 | Douglas | ............... A61M 5/2033 604/135 |
| 4,561,856 | A * | 12/1985 | Cochran | ............... A61M 5/155 604/143 |
| 6,419,662 | B1 * | 7/2002 | Solazzo | ............... A61M 3/0241 604/248 |
| 6,544,228 | B1 * | 4/2003 | Heitmeier | ......... A61M 5/16827 340/3.5 |

* cited by examiner

*Primary Examiner* — Brandy S Lee
*Assistant Examiner* — Hong-Van N Trinh
(74) *Attorney, Agent, or Firm* — Kirton McConkie; Brian Tucker

(57) ABSTRACT

A medical infusion pump can be configured to sequentially inject solutions from multiple syringes. The medical infusion pump can be configured to automatically sequence the injection either by creating differential fluid pressures during injection or by employing a sequencer that creates differential forces on poppets which form seals between different input ports of the sequencer.

20 Claims, 26 Drawing Sheets

MEDICAL INFUSION PUMP FOR SEQUENTIALLY INJECTING SOLUTIONS FROM MULTIPLE SYRINGES

CROSS-REFERENCE TO RELATED APPLICATIONS

This application is a divisional of U.S. patent application Ser. No. 14/856,091 which was filed on Sep. 16, 2015.

BACKGROUND

Some patients require repeated injections of a medication via an intravenous catheter. In such cases, it is common to insert a catheter prior to a first injection and then maintain the catheter within the patient's vasculature for use during subsequent injections. After a medication is administered through the catheter, the catheter is typically flushed with a saline solution to clear out any remaining medication and to maintain the catheter sterile. Also, to prevent clotting of blood within the catheter, the catheter is oftentimes flushed with an anticoagulant solution such as heparin.

In such scenarios, the medication, and possibly the saline solution and/or heparin (hereinafter collectively referred to as "solutions"), oftentimes must be injected at a specified rate. To facilitate injecting the solutions at the appropriate rate, injection pumps are used. An injection pump is a device that causes a solution to be injected into a patient's vasculature in accordance with a desired rate.

Some injection pumps, such as the Freedom60® infusion pump manufactured by RMS Medical Products which is shown in FIG. 5, are designed to receive a single syringe to which the patient's catheter is connected via tubing. These syringe-based injection pumps are commonly used for in-home injections. Such injection pumps are configured to apply a constant force to the syringe's plunger thereby causing the solution to continuously flow out from the syringe and into the tubing. To control the flow rate of the solution, tubing of an appropriate size can be selected.

One problem that exists with these syringe-based injection pumps is that, when solutions from multiple syringes must be injected, the administrator of the solutions must perform the injection process for each syringe. For example, if the patient required the sequential injection of a medication, a saline solution, and heparin, the administrator would first have to load the medication syringe into the injection pump, connect the medication syringe to the catheter, and start the injection process. Then, once the injection pump had fully dispensed the medication, the administrator would have to disconnect the medication syringe from the catheter and attach the saline syringe to separately administer the saline solution (which is typically performed directly without an infusion pump but could also be done using an infusion pump if desired). Finally, after the saline solution is administered, the administrator would have to disconnect the saline syringe from the catheter and connect the heparin syringe to inject the heparin (which is also typically performed directly without an infusion pump but could also be done using an infusion pump). This process can require a substantial amount of time especially if the required injection rate of the medication is slow.

In these situations, if the administrator was not able to switch out the syringe to initiate the next stage of the injection (e.g., if the administrator fell asleep while administering the solutions at night), the catheter could become unusable without further action. For example, if the saline solution and heparin are not injected, clotting may occur within the catheter that prevents further injections through the catheter. In such cases, the catheter may have to be replaced which typically requires visiting the hospital or other medical facility. Even if the clotting is minimal or if no clotting occurs, without proper flushing, the catheter may become contaminated thereby increasing the risk of infection or discomfort to the patient.

BRIEF SUMMARY

The present invention extends to a medical infusion pump for sequentially injecting solutions from multiple syringes. The medical infusion pump can be configured to house a number of syringes. To cause the solution of the syringes to be sequentially injected, the pump can employ pneumatic pistons of different sizes to apply a force on the plungers of the syringes. Due to the different sizes of the pistons, when an equal air pressure is applied to each piston, different forces will be applied to each plunger. The different forces will cause the solutions within the syringes to be ejected at different pressures. Tubing can then be used to couple the flow of the solutions into a common tube. The solution that is ejected at the highest pressure will be caused to flow through the common tube first followed sequentially by the solutions that are ejected at lower pressures.

Accordingly, to sequentially administer the solutions, the administrator needs only to pressurize the pump and initiate the process by releasing the pressure into the pistons. The injection of the solutions will then proceed sequentially without requiring further involvement. The present invention can therefore facilitate the administration of sequential solutions and minimize the likelihood that a catheter will become clotted or otherwise contaminated.

In one embodiment, a medical infusion pump for sequentially injecting solutions from multiple syringes comprises a housing having a first cradle and a second cradle that are each configured to receive a syringe, a first set of one or more pistons positioned along the first cradle, and a second set of one or more pistons positioned along the second cradle. Each of the one or more pistons in the first set has a piston rod that is connected to a first bridge. The first bridge is configured to contact a plunger of a first syringe when the first syringe is positioned within the first cradle such that, as the one or more pistons in the first set are actuated, the first bridge applies a force to a plunger of the first syringe. Each of the one or more pistons in the second set has a piston rod that is connected to a second bridge. The second bridge is configured to contact a plunger of a second syringe when the second syringe is positioned within the second cradle such that, as the one or more pistons in the second set are actuated, the second bridge applies a force to a plunger of the second syringe. A size of the one or more pistons in the first set is greater than a size of the one or more pistons in the second set such that when a pressure is applied to each piston in the first and second sets, the force applied by the first bridge to the plunger of the first syringe is greater than the force applied by the second bridge to the plunger of the second syringe thereby causing a first solution that exits the first syringe to have a greater pressure than a second solution that exits the second syringe.

In other designs, a medical infusion pump can be configured to employ a sequencer. The sequencer can include a number of input ports and an output port. A poppet can be positioned between input ports and configured with a larger surface area on its downstream side than on its upstream side. This differential surface area can create a net upstream force to block flow of solution from upstream-connected syringes while solution from a downstream-connected syringe is being injected. When a sequencer is employed, the medical infusion pump can employ syringe pumps that each inject solution from a syringe without requiring that the pumps employ specific forces. In particular, due to the poppets, proper sequencing can still be achieved even when the solution pressure created by the syringe pumps varies. Therefore, in such embodiments, a medical infusion pump can be designed with less stringent requirements.

In one embodiment, the present invention is implemented as a medical infusion pump for sequentially injecting solutions from multiple syringes that comprises multiple syringe pumps and a sequencer. Each syringe pump can be configured to receive a syringe and apply a substantially constant force on the syringe to cause a solution within the syringe to be ejected into tubing coupled to the syringe. The sequencer can have multiple input ports to which the syringes are coupled via the tubing and an output port. Each of the input ports and the output port are in fluid communication with a lumen. The sequencer further includes a poppet positioned within the lumen between each adjacent pair of the input ports. Each poppet includes a downstream side and an upstream side. The downstream side has a larger surface area than the upstream side. The larger surface area of the downstream side causes a solution, which is injected through one of the input ports downstream of the poppet, to apply a net upstream force on the poppet. The poppet is configured to form a seal against the lumen when the net upstream force is applied to the poppet. The seal prevents fluid from flowing downstream around the poppet.

This summary is provided to introduce a selection of concepts in a simplified form that are further described below in the Detailed Description. This Summary is not intended to identify key features or essential features of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
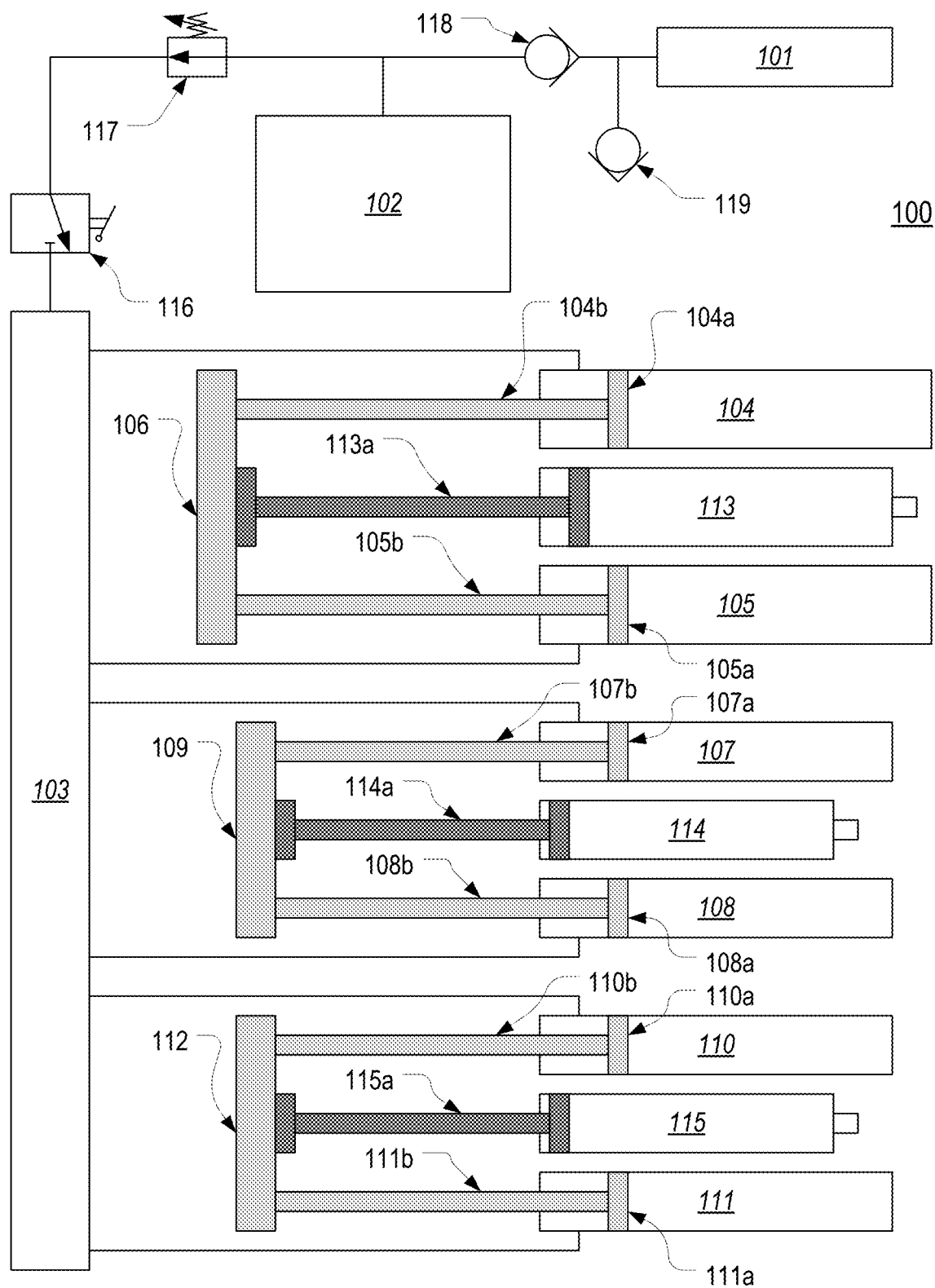
FIG. 1 illustrates a schematic of an example medical infusion pump for sequentially injecting solutions from multiple syringes in accordance with one or more embodiments of the present invention.
Figure 4A:
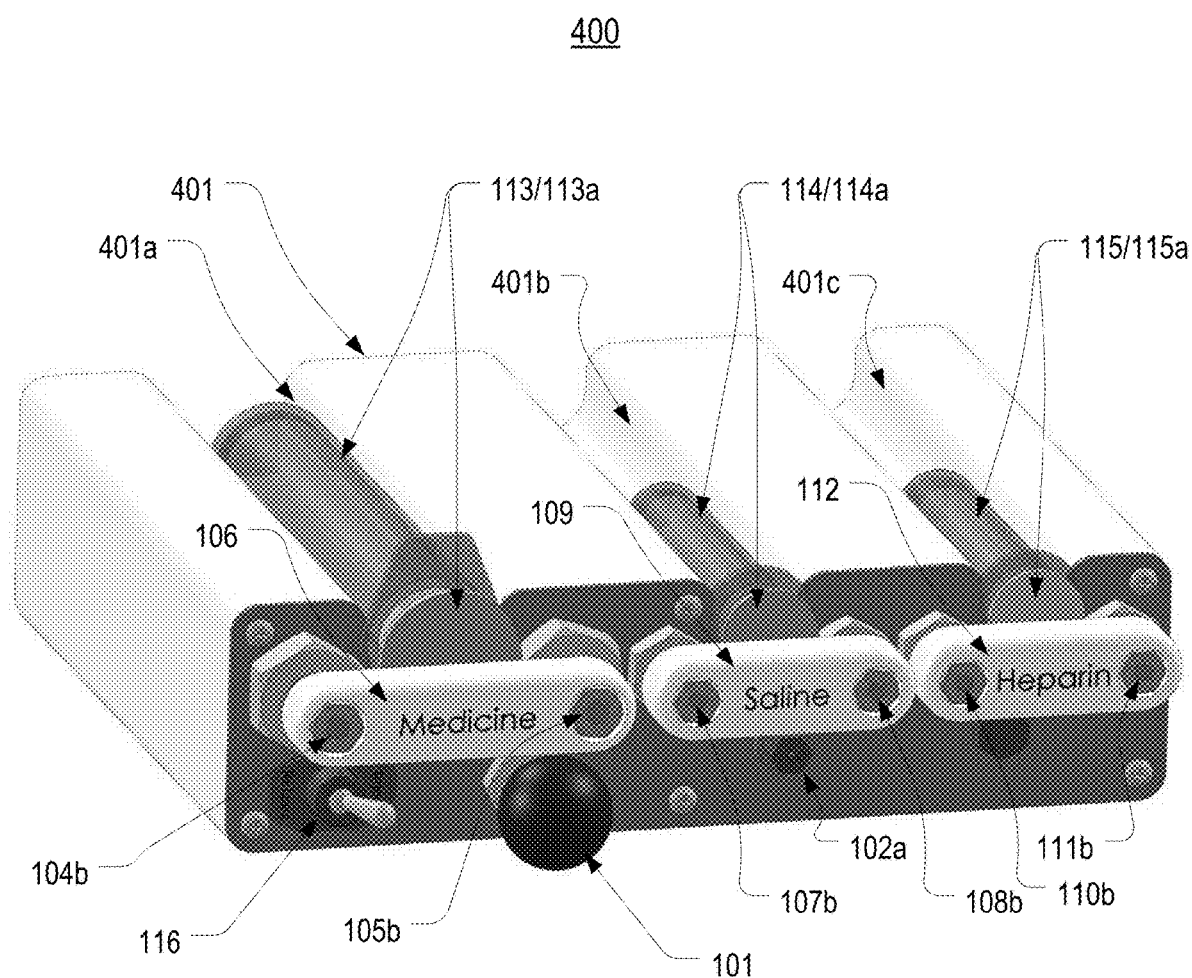
FIGS. 4A and 4B illustrate a front perspective view and a bottom perspective view respectively of an example medial infusion pump in accordance with one or more embodiments of the present invention.
Figure 4B:
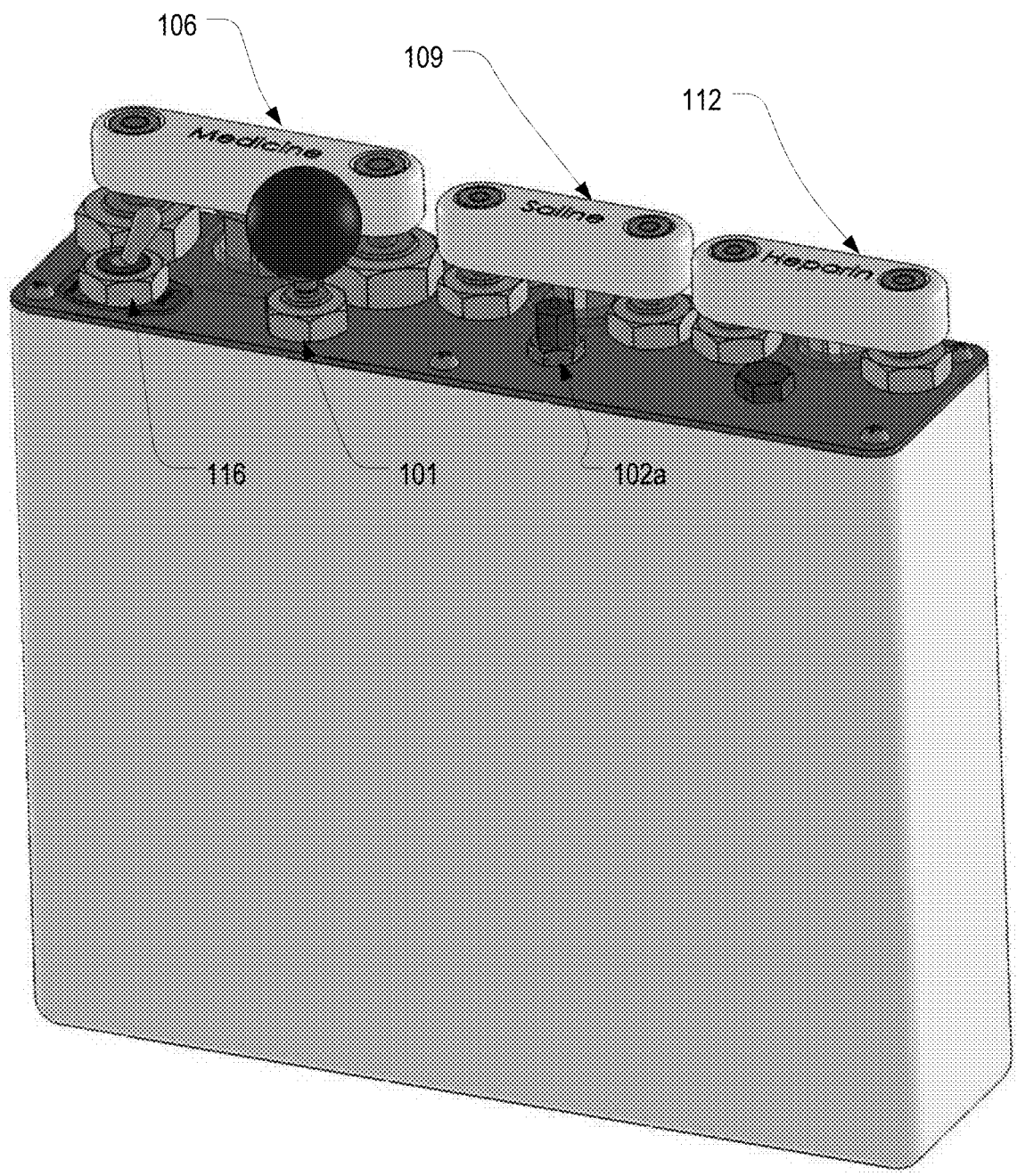

FIG. 1 illustrates a schematic of an example medical infusion pump 100 for sequentially injecting solutions from multiple syringes in accordance with one or more embodiments of the present invention. A housing (not shown) can be configured with three cradles for holding syringes 113-115. The components of infusion pump 100 can be contained with the housing to form a unitary pump structure such as is shown in FIGS. 4A and 4B.

Infusion pump 100 includes a storage tank 102 for storing compressed air. Although a single storage tank is shown, multiple storage tanks could be combined to provide sufficient storage capacity. A pump 101 can be used to compress air into storage tank 102. In preferred embodiments, a manual pump can be employed so that infusion pump 100 can be operated completely without an external source of energy. However, in some embodiments, an electric pump may be employed. In some embodiments, check valves 118, 119 can be employed to block backwards flow of air absent excess pressure in the storage tank.

Storage tank 102 can be coupled to a manifold 103 via a valve 116. In some embodiments, a pressure regulator 117 may be coupled between storage tank 102 and manifold 103 to limit the amount of pressure that is supplied from storage tank 102. Manifold should be construed broadly to encompass any structure for routing air from storage tank 102 to multiple destinations.

Manifold 103 distributes the compressed air to three sets of cylinders (104, 105, 107, 108, 110, 111). A first set of cylinders 104, 105 are positioned on opposite sides of a first cradle in which syringe 113 is held. A second set of cylinders 107, 108 are positioned on opposite sides of a second cradle in which syringe 114 is held. A third set of cylinders 110, 111 are positioned on opposite sides of a third cradle in which syringe 115 is held. FIG. 4A depicts an example of how these cradles can be configured.

Each cylinder includes a piston (104a, 105a, 107a, 108a, 110a, 111a) and a piston rod (104b, 105b, 107b, 108b, 110b, 111b). A first bridge 106 can be coupled between piston rods 104b, 105b, a second bridge 109 can be coupled between piston rods 107b, 108b, and a third bridge 112 can be coupled between piston rods 110b, 111b. As shown, because the sets of cylinders are positioned on opposite sides of the cradles, the bridges will be positioned to apply a force against the plungers of the syringes when the pistons are actuated.

To actuate the pistons, valve 116 can be opened to allow the compressed air to pass from storage tank 102 into each of the cylinders. The compressed air will then apply a force against each of the pistons. In accordance with embodiments of the present invention, the size of the cylinders can be configured to cause bridge 106 to apply a greater force than bridges 109, 112, and to cause bridge 109 to apply a greater force than bridge 112. These differences in forces will cause the solution within syringe 113 to be ejected at a higher pressure than the solutions in syringes 114, 115. Similarly, the solution in syringe 114 will be ejected at a higher pressure than the solution in syringe 115. These differences at which the solutions are ejected from the syringes will cause the solutions to be injected in a sequential manner.

Figure 2:
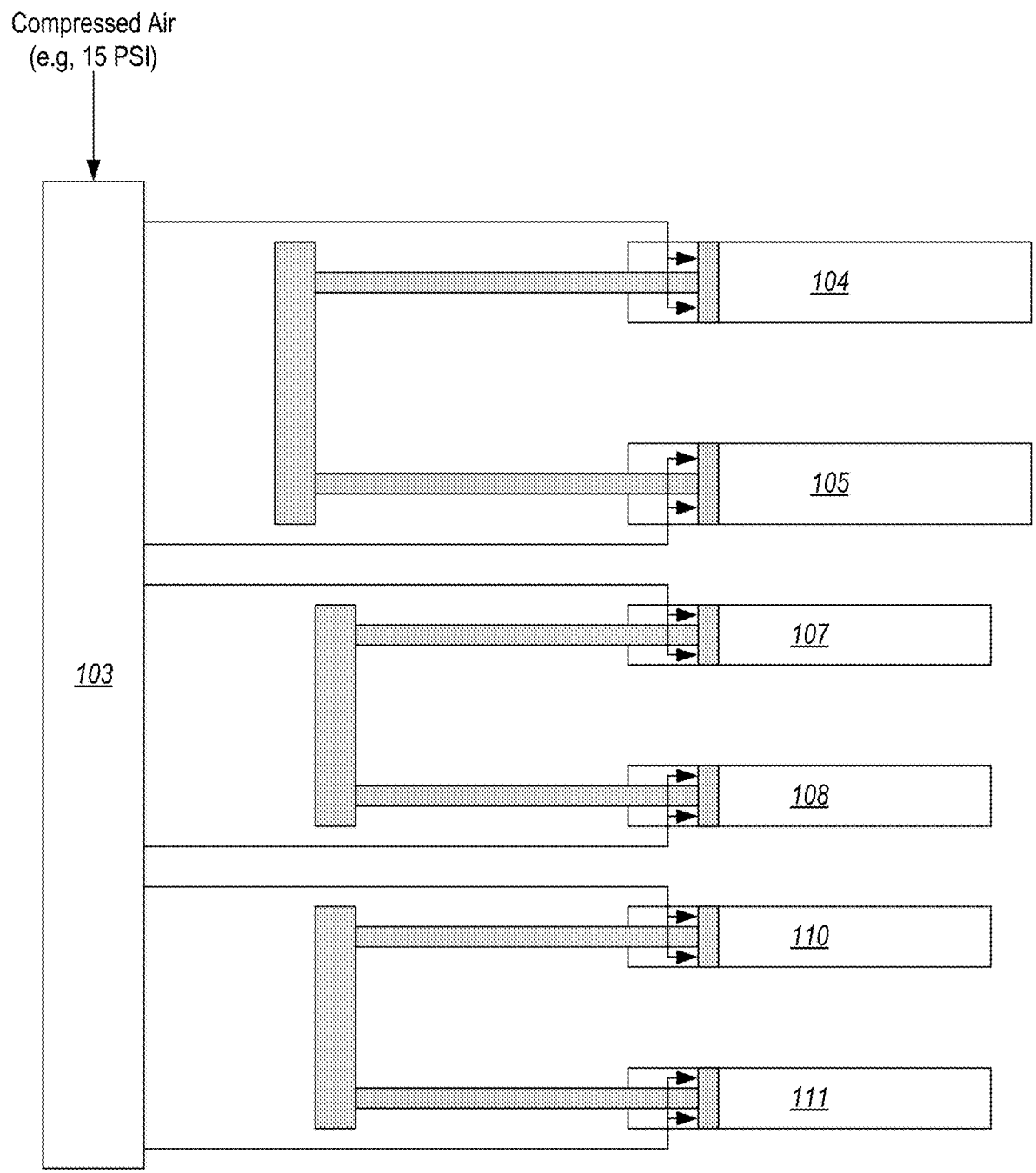
FIG. 2 illustrates a portion of the schematic of FIG. 1 showing how the pistons of the example medical infusion pump apply a force to syringes.

FIG. 2 illustrates a portion of the schematic of FIG. 1 that includes manifold 103 and the components of cylinders 104, 105, 107, 108, 110, 111. As shown, when compressed air (e.g., at 15 PSI) is released into manifold 103, the compressed air will cause a pressure to be applied to the surface of each piston as represented by the arrows. This pressure will be substantially equal within each cylinder. However, because the size (or surface area) of the pistons is not equal, the force that results from this pressure will vary among cylinders. For example, the first set of cylinders 104, 105 have a greater diameter than the other cylinders. Given that the force applied to a piston is based on the equation Force=Pressure*Area, the force applied on pistons 104a, 105a will be larger than the force applied on the other smaller pistons. As a result, the force applied by bridge 106 on syringe 113 will be greater than the force applied by bridges 109, 112 on syringes 114, 115. Similarly, the second set of cylinders 107, 108 have a greater diameter than cylinders 110, 111. Therefore, the force applied by bridge 109 will be greater than the force applied by bridge 112.

FIGS. 3A-3H illustrate how these different forces cause syringes 113-115 to sequentially eject their solutions. In these figures, syringe 113 contains a solution 310, syringe 114 contains a solution 320, and syringe 115 contains a solution 330. As an example, solution 310 can be a medication, solution 320 can be saline, and solution 330 can be heparin. The ejection port of syringe 113 is connected via tubing 301a to a first input of coupler 302a. Similarly, the ejection ports of syringes 114, 115 are connected via tubing 301b, 301c to opposite inputs of coupler 302b. Tubing 301d then couples the output of coupler 302b to the second input of coupler 302a. Finally, the output of coupler 302a can be connected via tubing to a catheter or other means for intravenously administering the solutions.

Figure 3A:
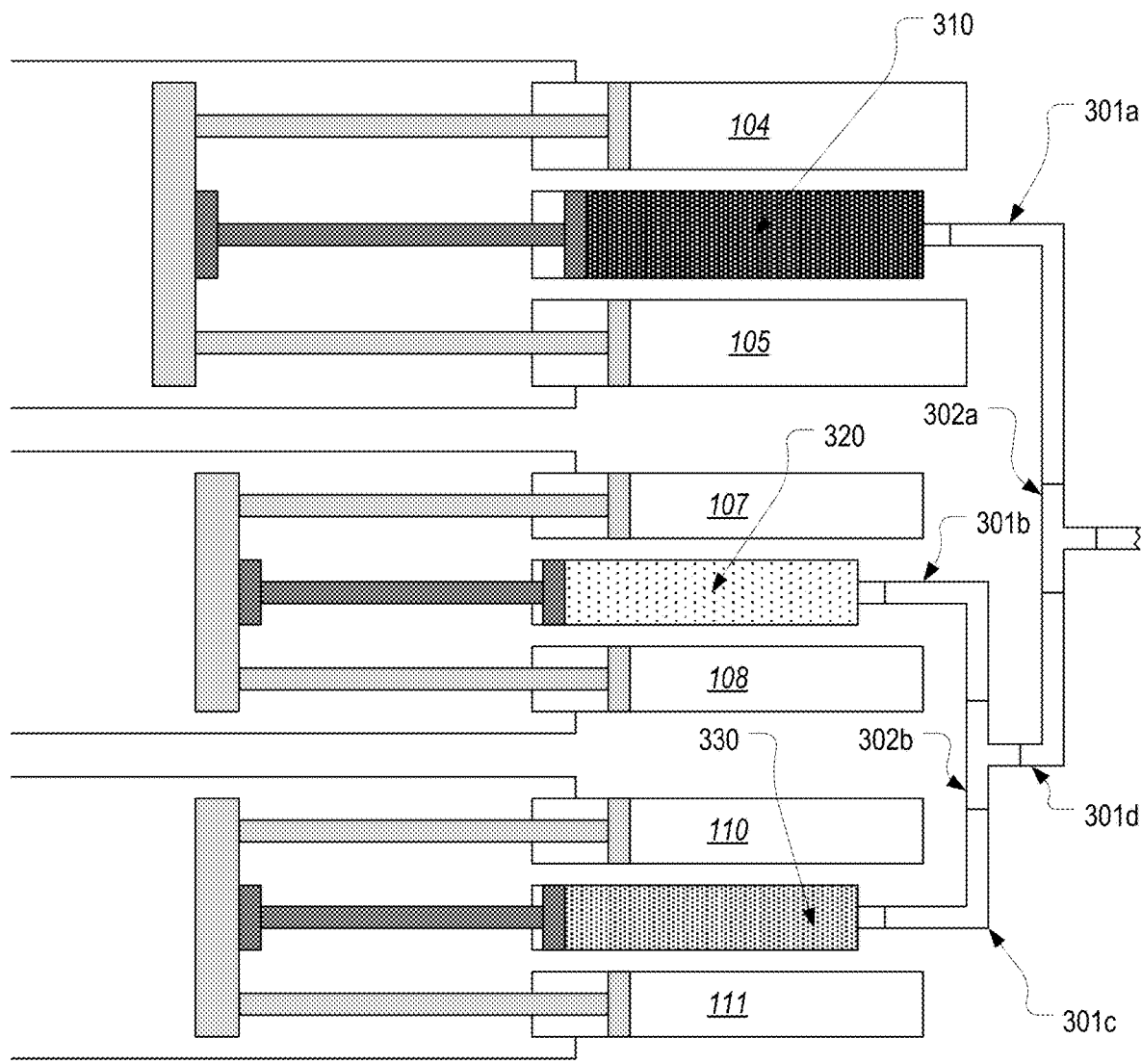
FIGS. 3A-3H illustrate a sequence of positions of the pistons of the example medical infusion pump of FIG. 1 when an equal pressure is applied to each piston.
Figure 3B:
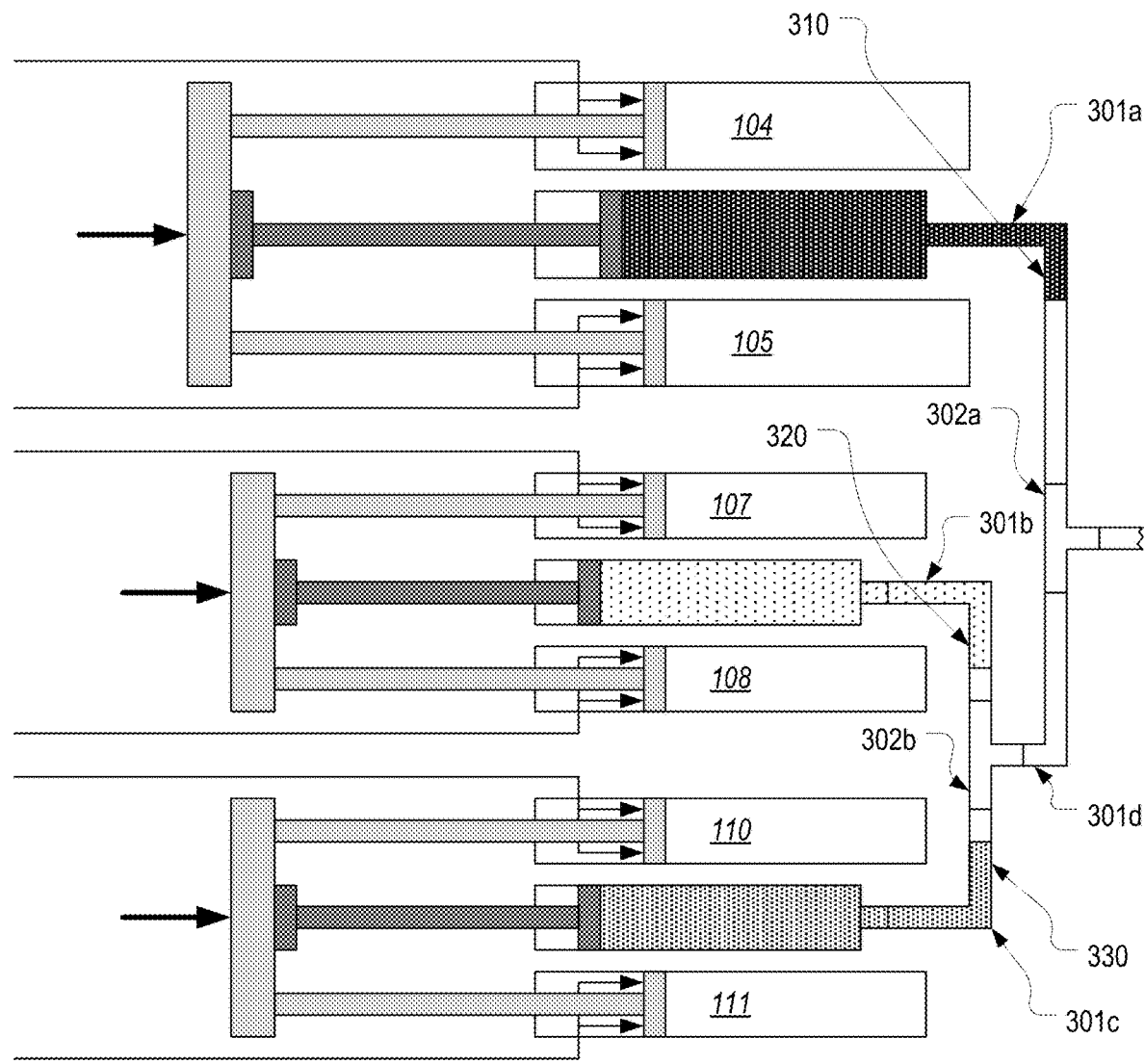

FIG. 3A represents the state of infusion pump 100 prior to valve 116 being opened. In this state, the pressure inside of the cylinders will be substantially the same as the external air pressure, and therefore, bridges 106, 109, 112 will not apply a force against plungers 113a-115a, and solutions 310, 320, 330 will remain within syringes 113-115. Next, FIG. 3B represents the state of infusion pump 100 a short time after valve 116 has been opened. As shown, once valve 116 is opened, compressed air fills the cylinders therefore creating a force against the pistons. As stated above, the force is dependent on the size (or surface area) of the pistons. Accordingly, the force applied to bridge 106 is greater than the force applied to bridge 109 which is greater than the force applied to bridge 112. Because tubing 301a-301d is initially empty, solutions 310, 320, 330 will commence flowing out through the tubing in response to these forces.

Figure 3C:
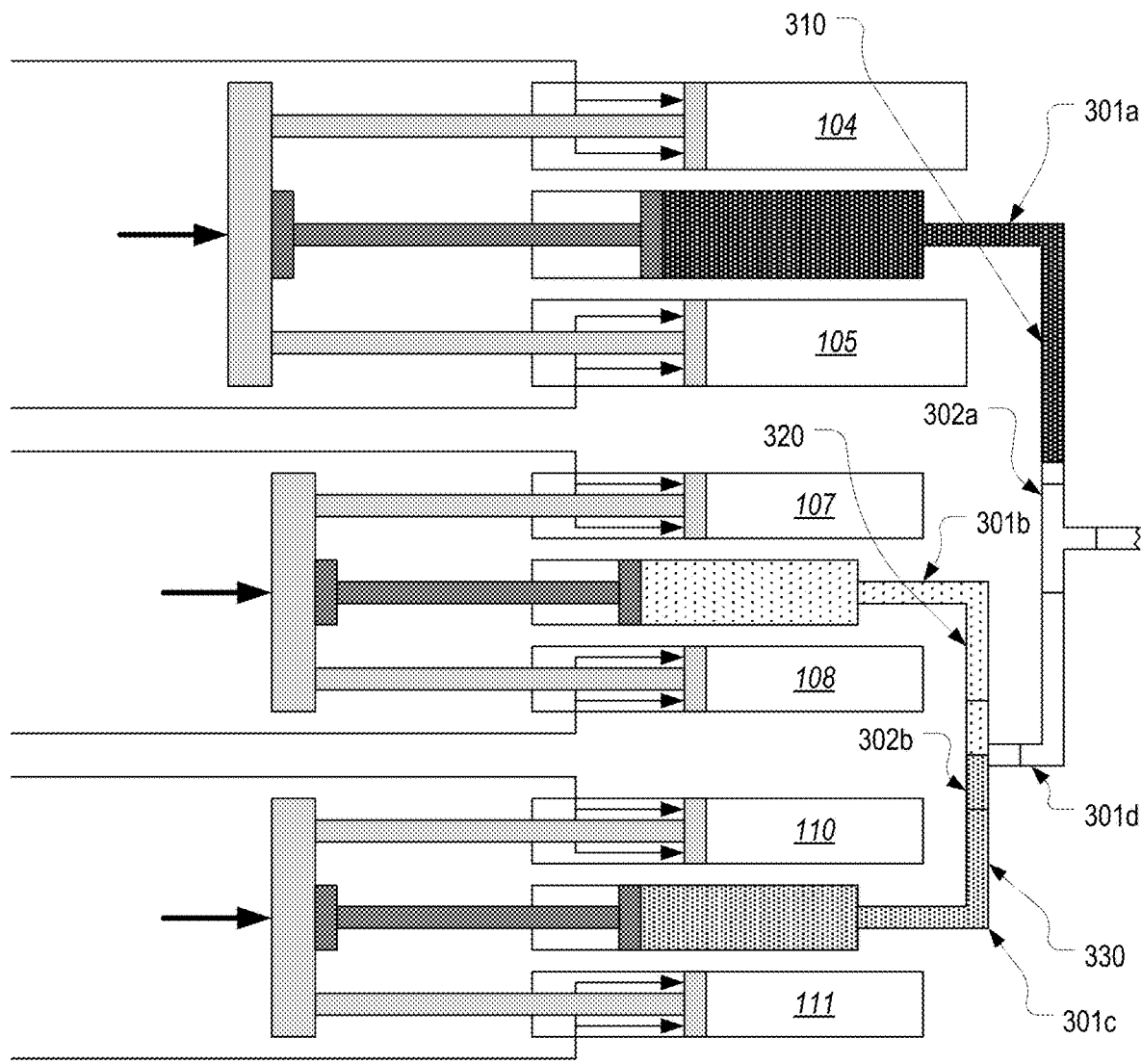

However, because the forces applied to bridges 106, 109, 112 are different, the pressure of solutions 310, 320, 330 within the tubing will also differ. The differences in the pressures of solutions 310, 320, 330 cause the solutions to be injected sequentially. In particular, as shown in FIG. 3C, solutions 320, 330 will flow through tubing 320, 330 until the solutions meet at some point. The depiction of the solutions meeting at the output of coupler 302b is an example only. The solutions may meet at any point along the tubing. Also, in some cases, the solutions may not actually meet such as when trapped air exists between the solutions. In the following discussion, any reference to solutions meeting should be construed as including instances where the solutions do not actually contact one another.

Regardless of the point at which the solutions meet, the greater pressure of solution 320 will prevent solution 330 from continuing to flow. In other words, the force applied by solution 320 against solution 330 (which is translated into a force against plunger 115a) will balance out the force applied by bridge 112 thereby preventing bridge 112 from forcing additional solution 330 from syringe 115.

Figure 3D:
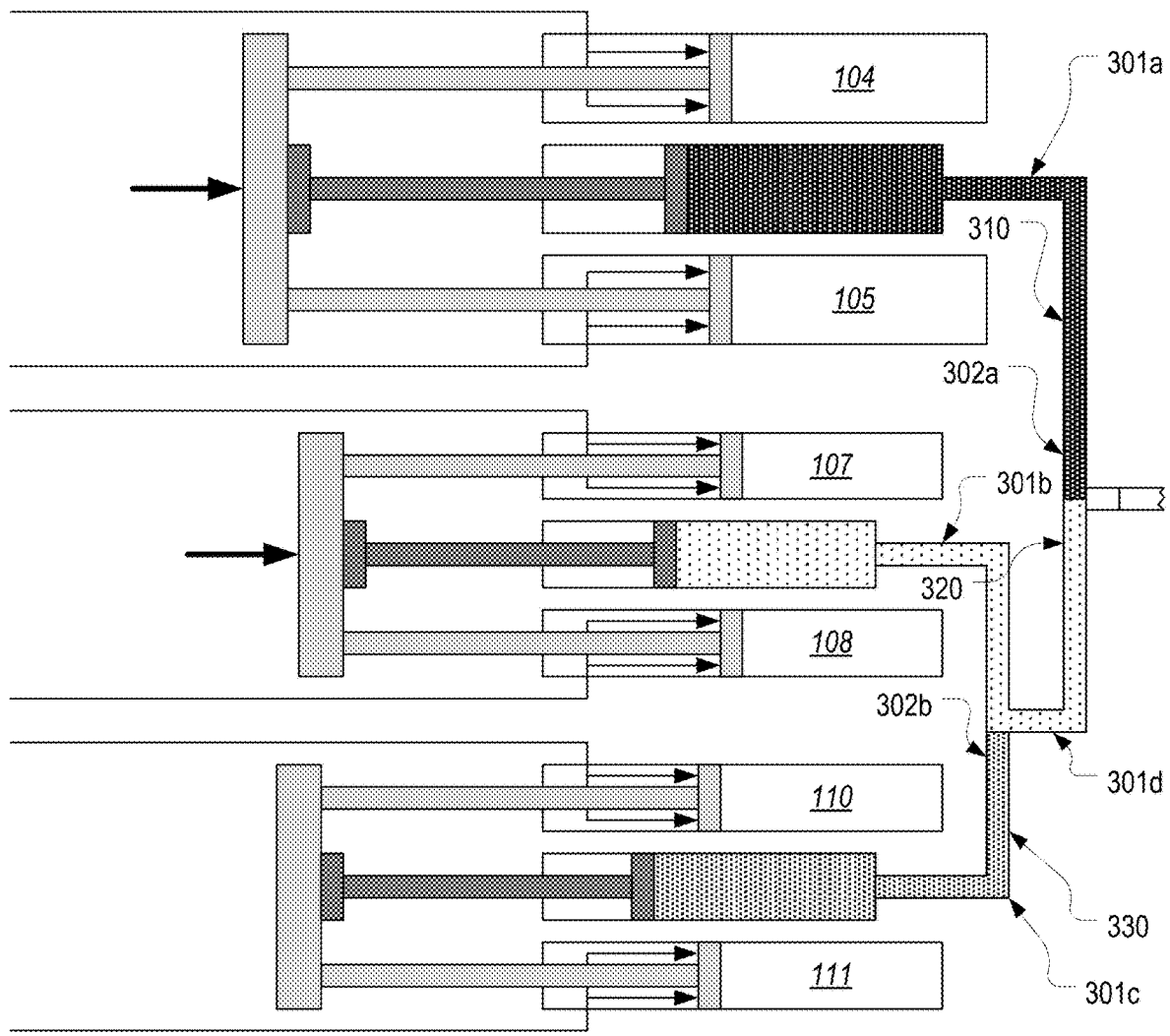
Figure 3E:
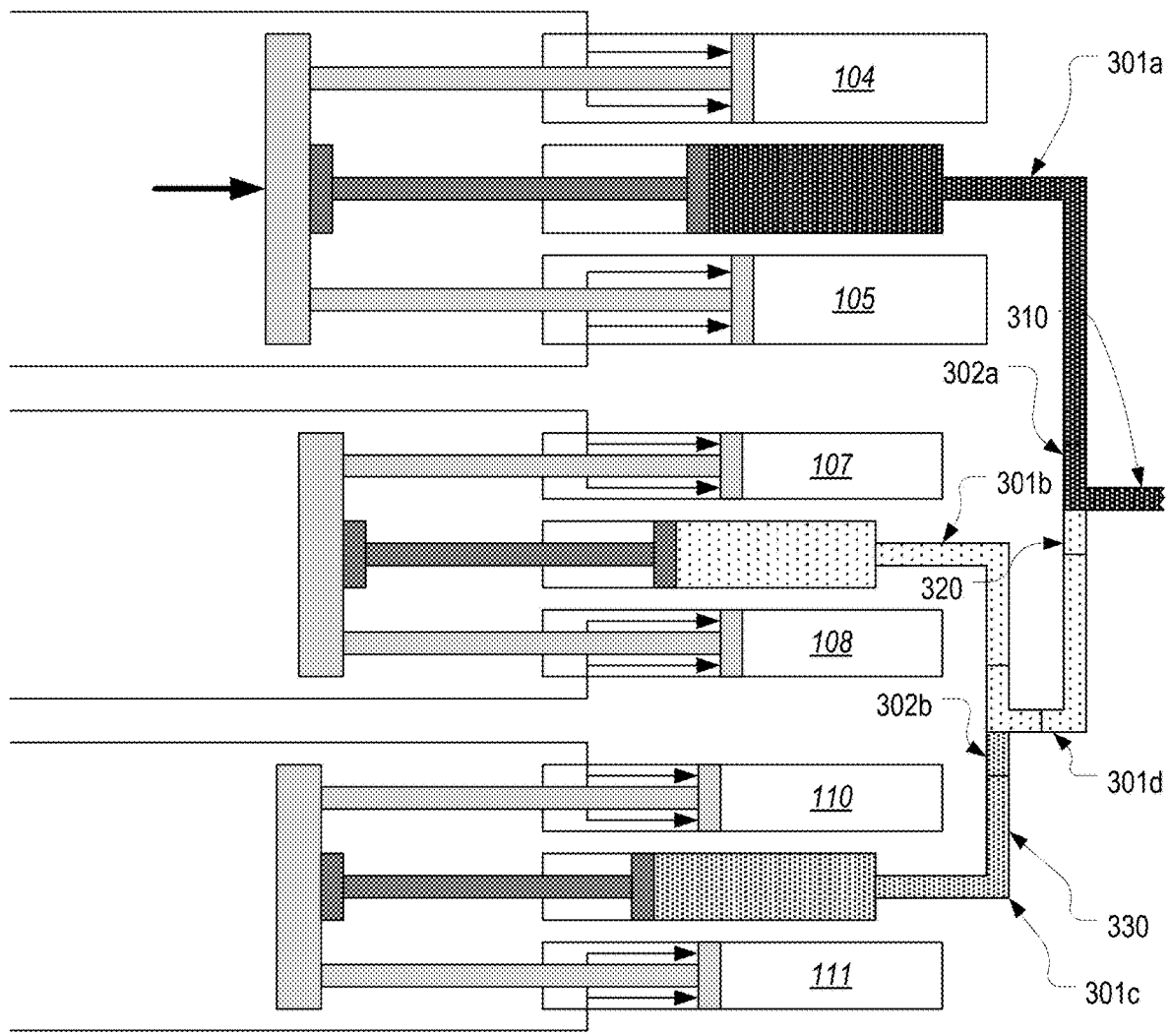

Accordingly, as shown in FIG. 3D, solution 320 will continue to flow through tubing 301d while solution 330 remains within syringe 115. At the same time, solution 310 will continue to flow through tubing 301a (and possibly out through coupler 302a or into tubing 301d). At some point (which is shown in FIG. 3D as the output of coupler 302a as an example only), solutions 310, 320 will meet. As described above, the greater pressure of solution 310 will prevent solution 320 from continuing to flow. Accordingly, as shown in FIG. 3E, solution 310 will flow out through coupler 302a and into the patient. The flow of solution 310, and therefore the blockage of solutions 320, 330 will continue until syringe 113 is substantially empty (i.e., until the pressure of solution 310 has fallen below the pressure of solution 320).

Figure 3F:
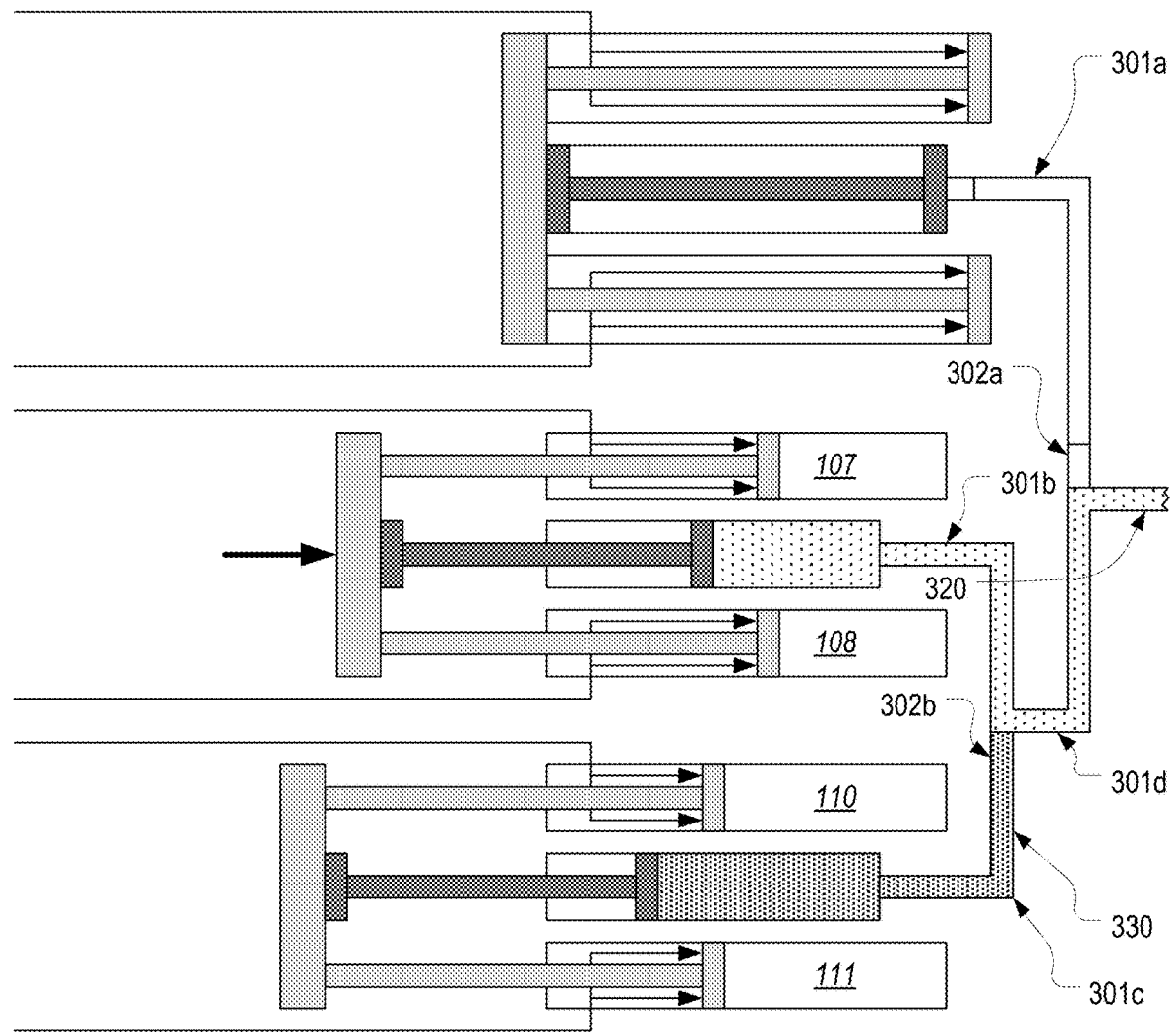

As shown in FIG. 3F, bridge 106 has fully compressed plunger 113a into syringe 113 and therefore solution 330 ceases flowing from syringe 113. At this point, with solution 310 no longer applying a force against solution 320 to prevent its flow, bridge 109 will commence compressing plunger 114a into syringe 114 thereby causing solution 320 to commence flowing out through coupler 302a. Because the pressure of solution 320 remains greater than the pressure of solution 330, the flow of solution 330 will remain blocked until solution 320 has been fully injected.

Figure 3G:
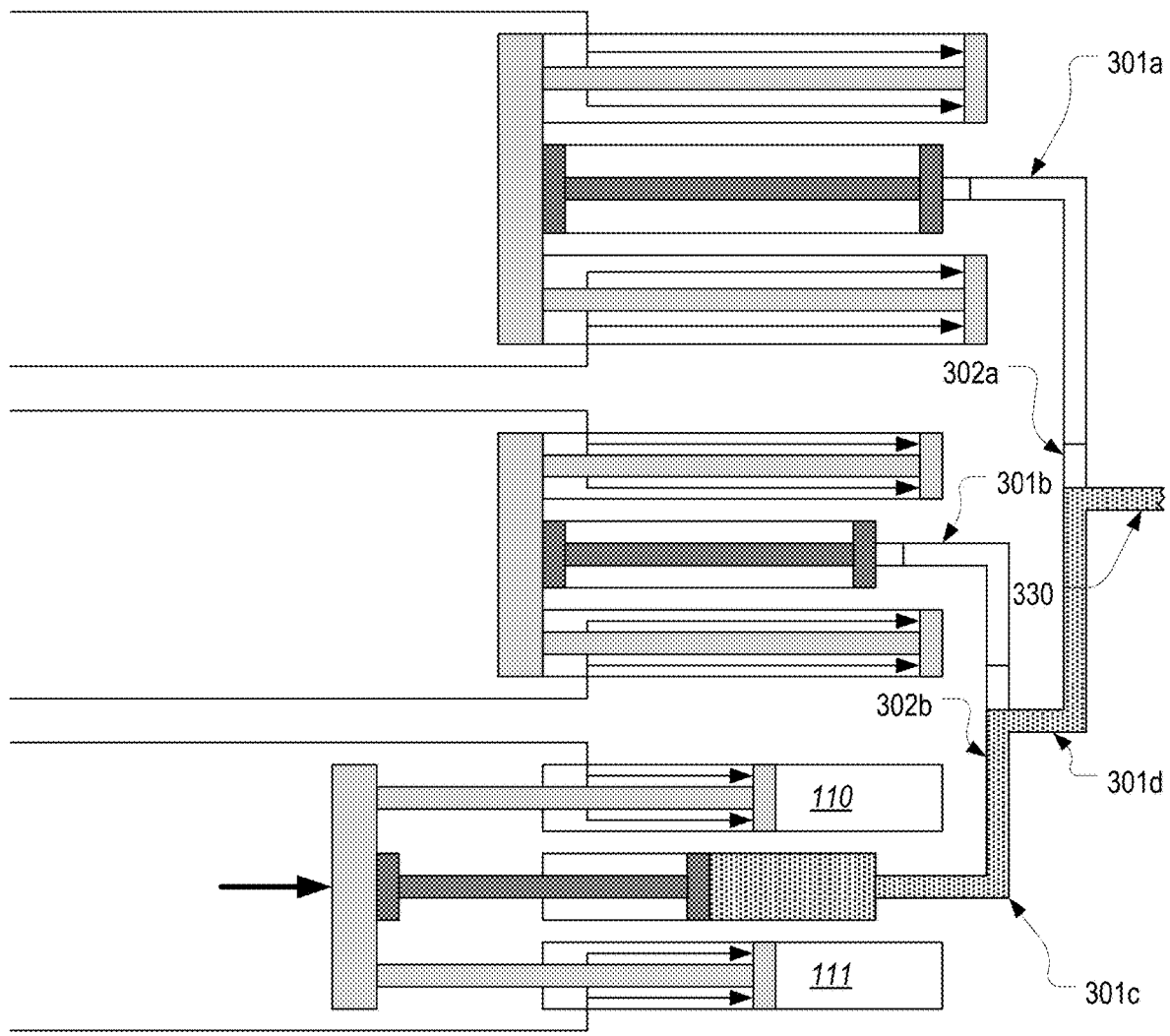
Figure 3H:
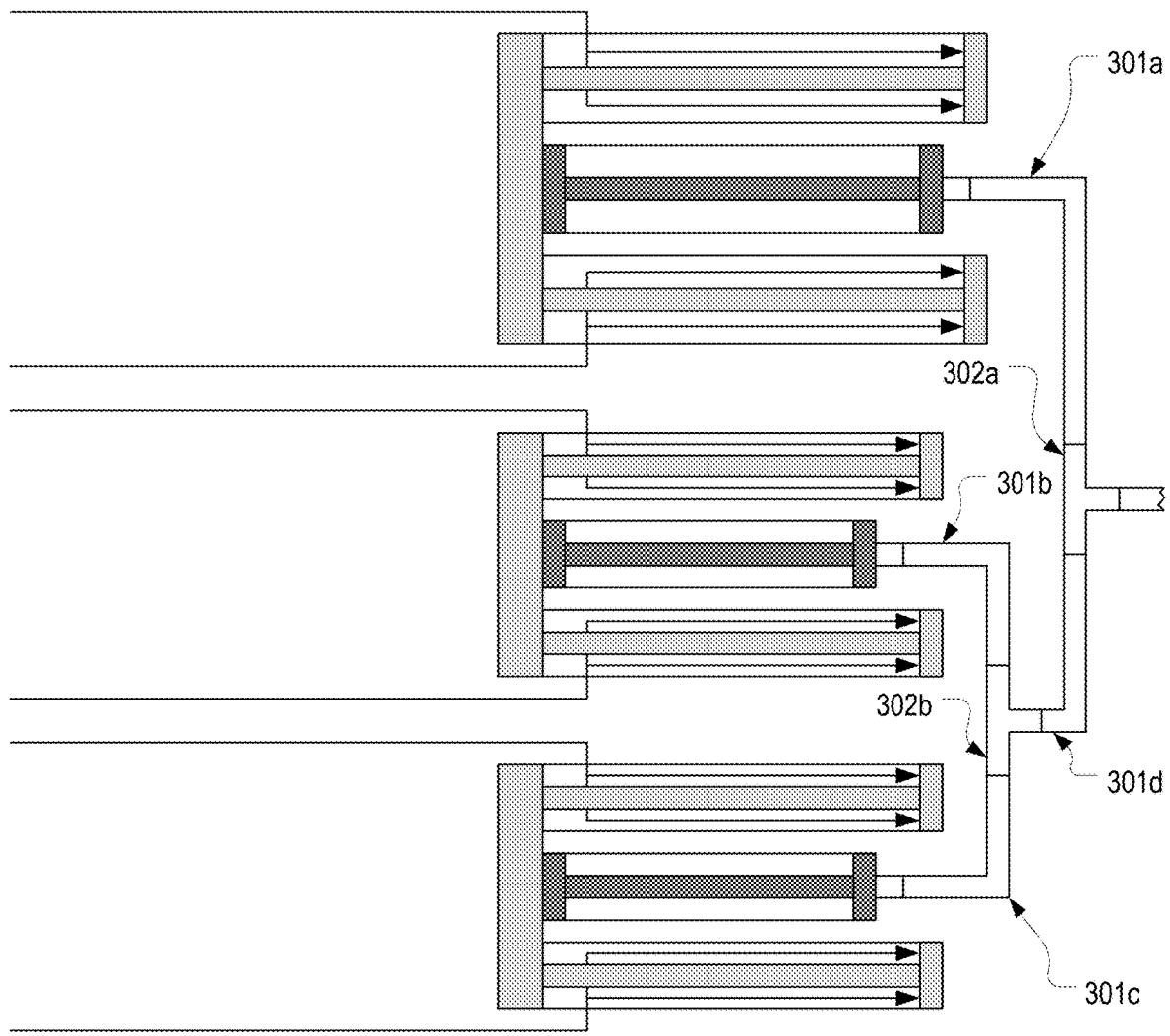

Once solution 320 has been fully injected, as shown in FIG. 3G, there will no longer be a force against solution 330 to offset the force of bridge 112. Therefore, bridge 112 will commence compressing plunger 115a to cause solution 330 to be injected. This will continue until solution 330 has been fully injected as shown in FIG. 3H.

Accordingly, by configuring the cylinders so that different forces are applied to the plungers, a sequence of injections can be obtained. Although this process has been described for a three syringe infusion pump, the same techniques can be employed with any multi-syringe infusion pump. For example, a two-stage, four-stage, or five-stage infusion pump could be configured to sequentially inject solutions. A five-stage infusion pump may be suitable for situations when two medications must be sequentially administered. For example, the first medication could be injected followed by a saline, the second medication, another saline, and heparin.

FIGS. 4A and 4B provide a three-dimensional model of a medical infusion pump 400 in accordance with one or more embodiments of the present invention. FIG. 4A illustrates a front perspective view while FIG. 4B illustrates a bottom perspective view. Infusion pump 400 can represent one embodiment of how the components of infusion pump 100 can be arranged. Accordingly, similar labels are used to identify the components that are visible in FIGS. 4A and 4B.

Infusion pump 400 comprises a housing 401 having three cradles 401a-401c. Cradles 401a-401c can have a diameter sufficient to contain the body of a syringe but small enough that the proximal lip of the syringe catches against the proximal opening of the cradle as shown. In this way, the syringe will be prevented from sliding along the cradle when the bridge applies a force to the plunger.

Infusion pump 400 is an example of an infusion pump that employs a set of two cylinders for each cradle. For example, for cradle 401a, piston rods 104b, 105b are shown extending out of housing 401 (within which cylinders 104, 105 are contained) and into bridge 106. Similarly, for cradle 401b, piston rods 107b, 108b are shown extending out of housing 401 and into bridge 109, while for cradle 401c, piston rods 110b, 111b are shown extending out of housing 401 and into bridge 112.

FIGS. 4A and 4B also depict valve 116 as having a switch that can be toggled between an inject (or open) position and a release (or closed) position. A pump 101 is also shown. Pump 101 can be configured to slide in and out to pump air into storage tank 102 (not visible). Infusion pump 400 also includes a pressure indicator 102a which provides a visual indication of the amount of pressure within storage tank 102. For example, pressure indicator 102a can include a component that extends outwardly once a certain level of pressure (e.g., 30 PSI) has been obtained within storage tank 102. Pressure indicator 102a can serve to notify the administrator when a sufficient quantity of air has been compressed into storage tank 102 to enable the injection process to be carried out. As described above, the use of pressure regulator 117 can ensure that the appropriate amount of pressure is applied to the cylinders even if excess pressure exists within storage tank 102.

To initiate the injection process using infusion pump 400, the administrator can set valve 116 to release (i.e., close the valve) to release the pressure from the pistons. With valve 116 set to release, the administrator can easily retract bridges 106, 109, 112 to allow the loaded syringes to be placed in cradles 401a-401c. It is noted that FIGS. 4A and 4B depict the state of infusion pump 400 after the injection process since the bridges have already fully compressed the plungers into the syringes. However, this state can be the same as the state of the infusion pump immediately prior to loading full syringes into the cradles.

In addition to retracting the bridges and placing the syringes in the cradles, the administrator can also attach the appropriate tubing to each syringe. The size of the tubing can be selected to control the rate at which the solutions will be injected. In particular, tubing having a smaller internal diameter will cause the solutions to flow more slowly than tubing having a larger diameter. The administrator may also use pump 101 to compress air into storage tank 102, such as, for example, until pressure indicator 102a indicates that sufficient pressure exists within storage tank 102.

After performing these steps, the administrator can then set valve 116 to inject which will cause the compressed air to be released into each cylinder thereby causing bridges 106, 109, 112 to commence applying a force against the corresponding plungers 113a-115a. At this point, the injection process can proceed without further involvement of the administrator. In particular, the different forces that are applied by bridges 106, 109, 112 will cause the solutions in syringes 113-115 to be injected sequentially as described above.

Although in the above description, each embodiment is described as employing two cylinders for each cradle, an infusion pump in accordance with the present invention could also be configured to use a single cylinder for each cradle. For example, cylinder 104 could be appropriately sized so that cylinder 105 is not necessary. In such a case, bridge 106 could be secured only to piston rod 104b, or a dummy rod could be used in place of piston rod 105b to provide added stability. Similarly, although the figures depict that each set of cylinders includes cylinders of the same size, in some embodiments, two differently sized cylinders could be employed within a single set. For example, cylinders 104, 105 could have different sizes as long as the total force created by the two cylinders equaled the necessary force to create the proper sequencing.

In one particular embodiment, the relative sizes of the cylinders can be configured so that the pressure at which each solution is ejected is at least 1.5 psi higher than the pressure of the next lowest syringe. For example, the size of cylinders 104, 105 can be configured to cause the solution in syringe 113 to be ejected at a pressure of 15 psi, the size of cylinders 107, 108 can be configured to cause the solution in syringe 114 to be ejected at 13.5 psi, and the size of cylinders 110, 111 can be configured to cause the solution in syringe 115 to be ejected at 12 psi. One of skill in the art will understand that there are various factors that influence the pressure at which a solution will be injected even when a constant pressure is applied to the pistons including the surface area of the piston that is exposed to the pressure (which is determined both by the size of the piston and the size of the piston rod), the amount of force required to overcome the friction between the piston and the inside surface of the cylinder, the amount of force required to overcome the friction between the plunger and the inside surface of the syringe, etc. These factors, among others, can be considered when deciding upon the configuration of a particular implementation of an infusion pump.

Figure 5:
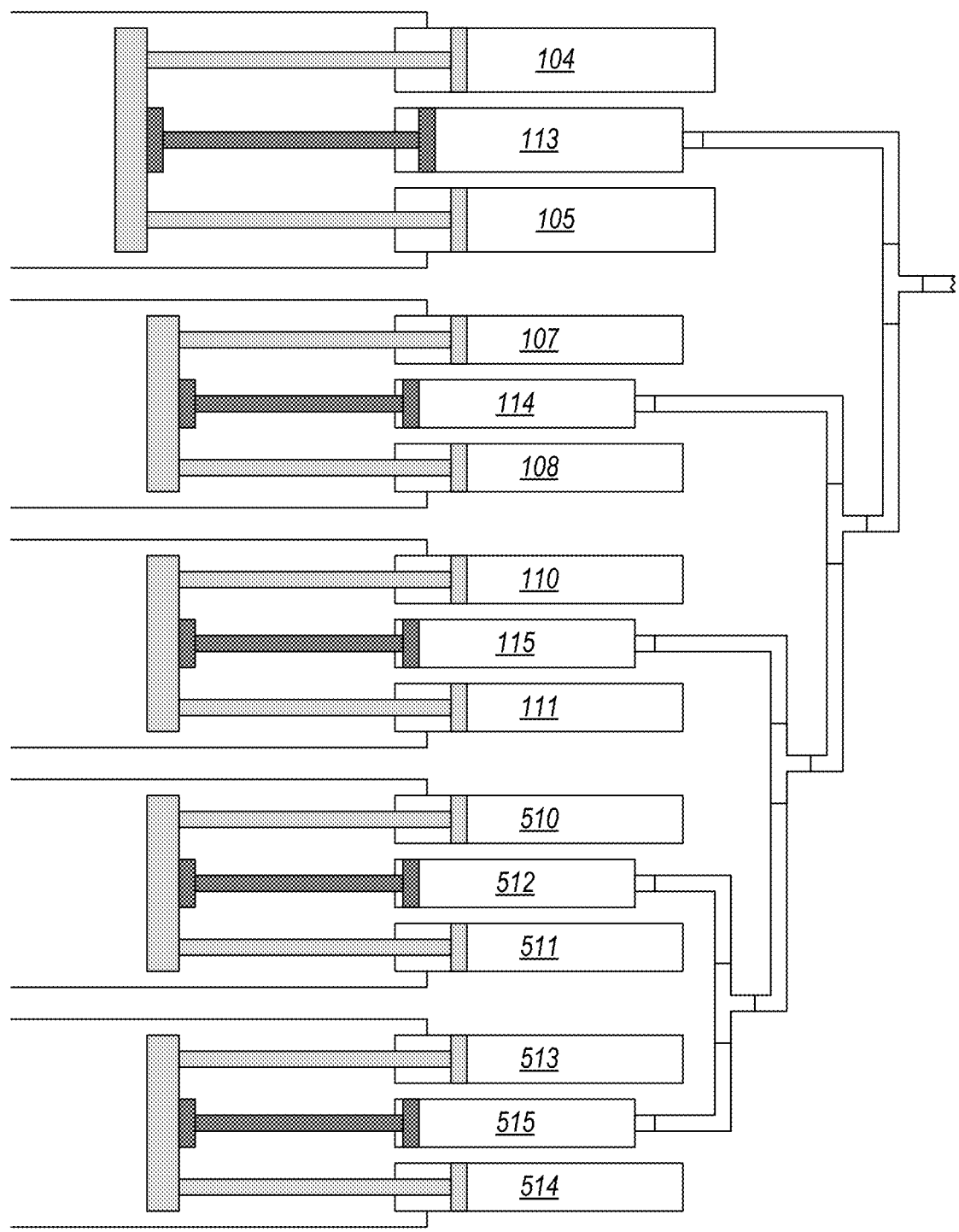
FIG. 5 illustrates a partial schematic of a five-stage infusion pump.
Figure 6:
FIG. 6 illustrates a prior art medical infusion pump that can be used to administer a solution from a single syringe.

FIG. 5 illustrates an example of how a five-stage infusion pump could be configured. As shown, in addition to the first three sets of cylinders depicted in FIG. 1, a fourth set of cylinders 510, 511, and a fifth set of cylinders 513, 514 are included to create the five-stage design. Additional tubing is employed to connect the five syringes using a cascading pattern as shown. This five-stage design would function in the same manner as described above with the solution in syringe 113 being injected first followed sequentially by the solutions in syringes 114, 115, 512, 513.

FIGS. 7-9F illustrate an alternative design of an infusion pump 700 in accordance with one or more embodiments of the present invention. Infusion pump 700 comprises a number of syringe pumps 700a-700c and a sequencer 710. Each of syringe pumps 700a-700c has a similar design that includes a housing 701, a cradle 702 which is slidably coupled to housing 701 via shafts 703, and a gas spring 704. As shown, each cradle 702 includes a channel 702a in which the body of a syringe can be placed during an infusion. An end of each shaft 703 can include a structure 703a to prevent cradle 702 from being separated from housing 701. Although each syringe pump is shown as being contained within a separate housing, the syringe pumps could also be contained within the same housing. However, by employing separate housings, infusion pump 700 can be easily configured with more or less than three syringe pumps.

Each gas spring 704 contains a rod 704a and a piston 704b. Piston 704b includes a channel 704c through which compressed gas (typically nitrogen) may flow during movement of piston 704b. An end 704d of rod 704a extends out through an opening (not shown) in housing 701. As will be described below, end 704d applies a force to the plunger of a syringe that is contained within cradle 702.

Due to the compressed gas within gas spring 704 as well as the differences in the surface area on each side of piston 704b, rod 704a will be biased towards an extended position.

Figure 7:
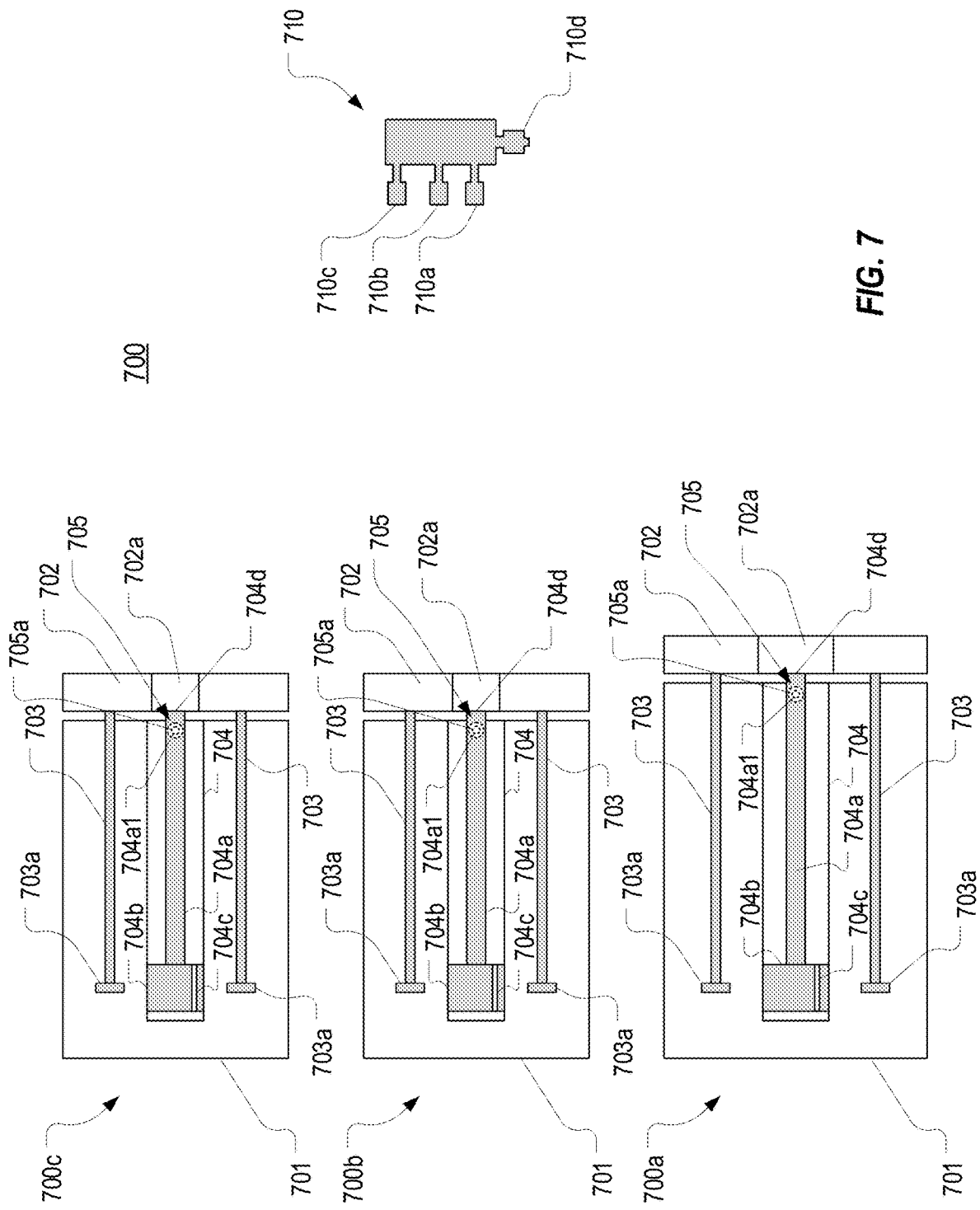
FIG. 7 illustrates a schematic of an example medical infusion pump that employs a sequencer.
Figure 7A:
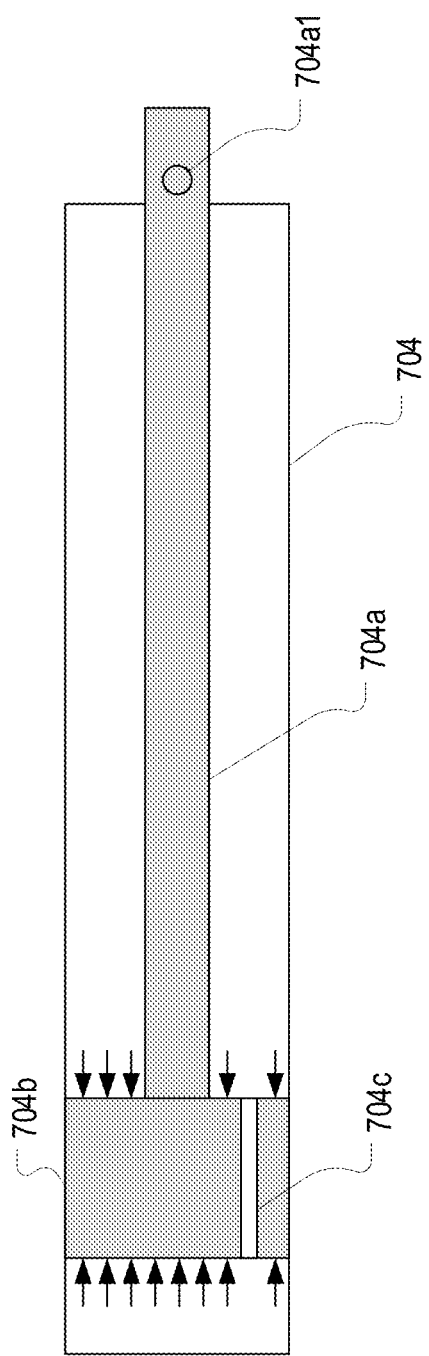
FIG. 7A illustrates a gas spring that can be employed within a syringe pump included in the medical infusion pump of FIG. 7.

FIG. 7A represents this concept. The force applied by the compressed gas on piston 704b is represented by the arrows. Because more surface area exists on the left side of piston 704b than on the right side of piston 704b, the compressed gas will force rod 704a to the right. In other words, to reach the position shown in FIG. 7A, an external force must be applied to rod 704a. Accordingly, in FIG. 7, each of syringe pumps 700a-700c is shown in a "loaded" state. To maintain them in this state, each syringe pump 700a-700c can include a locking structure 705. For example, each rod 704a may include a notch 704a1 into which a locking pin 705a can insert to retain rod 704a in the position shown in FIG. 7. This locking pin 705a can be coupled to housing 701 in such a way as to allow a user to release rod 704a from the locked position as will be further described below.

In FIG. 7, syringe pump 700a is shown as being larger than syringe pumps 700b and 700c. Such may be the case when syringe pump 700a is used to administer a medication while syringe pumps 700b and 700c are used to administer saline and heparin as described above. For example, syringe pump 700a may be configured to administer a medication from a 50 ml syringe while syringe pumps 700b and 700c may be configured to administer a medication from a 10 ml syringe. It is noted, however, that the present invention extends to embodiments where an infusion pump may include any number of syringe pumps of any size.

Each syringe pump can be configured to apply a substantially constant force on a syringe throughout the pump's stroke. This force can create a substantially constant fluid pressure in the downstream tubing. For example, each syringe pump may create a fluid pressure of approximately 1 bar (or 14.5 psi) within the downstream tubing. This is in contrast to infusion pump 100 which sequences the infusion based on differential fluid pressure. Because infusion pump 700 does not rely on fluid pressure differences, its design can be simpler than infusion pump 100.

To cause proper sequencing, infusion pump 700 includes sequencer 710. As shown in FIG. 7, sequencer 710 includes a number of input ports 710a-710c (which in this case is three to correspond to the number of syringe pumps) and an output port 710d. Sequencer 710 is configured to cause solution to be sequentially injected first through input port 710a, then through input port 710b, and finally through input port 710c.

Figure 8:
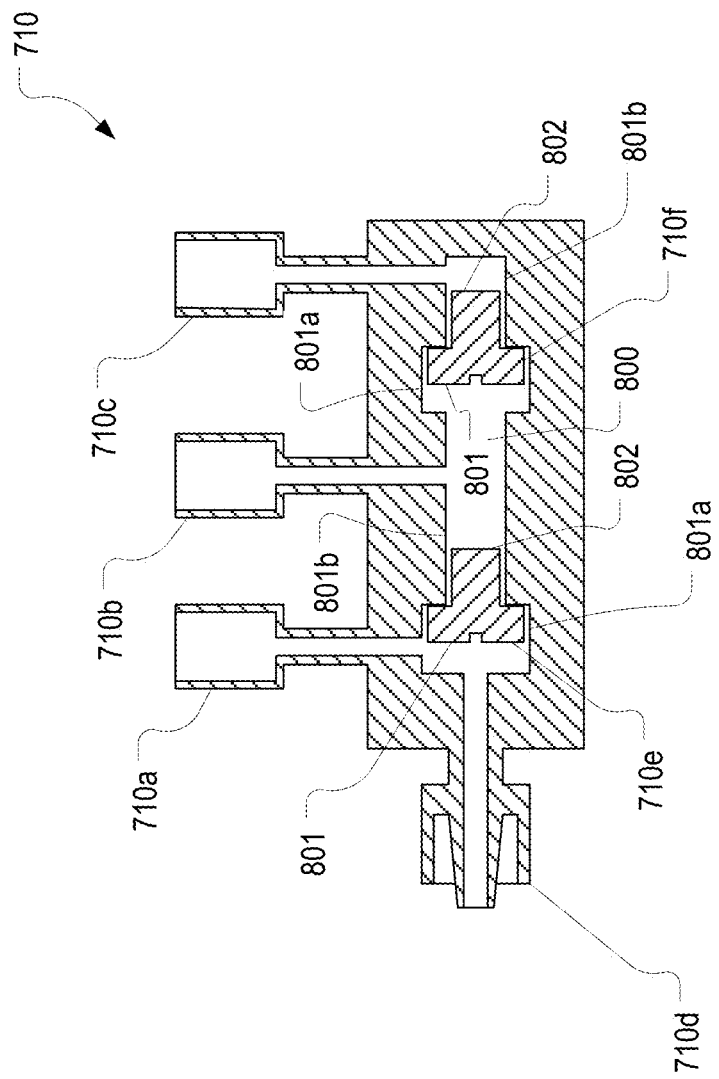
FIG. 8 illustrates a cross-sectional view of an example sequencer that can be employed in the medical infusion pump of FIG. 7.

FIG. 8 provides a cross-sectional view of sequencer 710 to illustrate how this sequencing is accomplished. Each of ports 710a-710d is in fluid communication with a common lumen 800. Lumen 800 is structured to contain poppets 710e, 710f. For purposes of this specification, a poppet should be construed as a flow-blocking structure having one side 801 with a greater frontal area and an opposite side with a lesser frontal area. The term frontal area should generally be construed as the surface area that is perpendicular to the axis of the poppet. When a pressurized solution is contained within a poppet, the pressure will apply a force against the poppet that is proportional to the frontal area. As shown in FIG. 8, the left side (or downstream side) 801 of each poppet has a larger frontal area than the right side (or upstream side) 802. For purposes of this specification, a side of a poppet should be construed as a portion of the poppet that is exposed to fluid pressure during infusion. As will be further described below, this difference in the frontal areas will therefore create a net upstream force when solution is present on both sides of the poppet.

Poppet 710e is positioned within lumen 800 between input ports 710a and 710b. The portion of lumen 800 that contains poppet 710e is structured to form a seal between the sidewall of lumen 800 and poppet 710e thereby substantially blocking fluid flow through this portion of lumen 800. Poppet 710f is similarly positioned within lumen 800 between input ports 710b and 710c. As shown, side 801 may include recesses or other features to increase the surface area differential between sides 801 and 802.

In some embodiments, such as is shown in FIG. 8, lumen 800 can include increased diameter regions 801a and reduced diameter regions 801b. Side 802 of the poppets can be configured with a smaller diameter than side 801. The reduced diameter regions 801b of lumen 800 can be large enough to contain side 801, but not side 801. The resulting ridge formed between regions 801a and 801b can therefore serve as a surface against which the poppets form a seal.

Figure 9A:
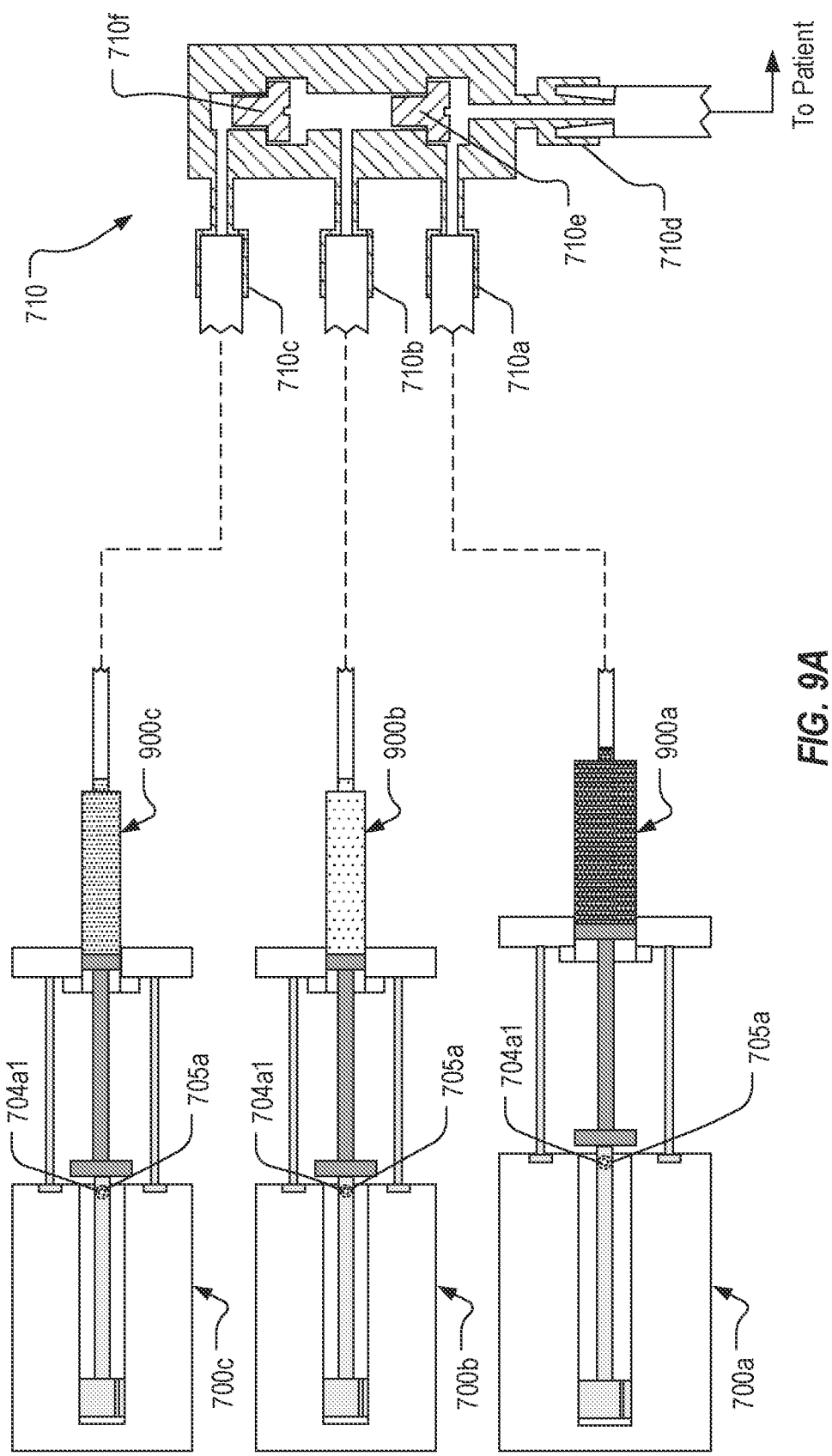
FIGS. 9A-9F illustrate a sequence of states of the medical infusion pump of FIG. 7 during an infusion.

FIGS. 9A-9F illustrate how infusion pump 700 functions. It is noted that these figures are not drawn to scale. In FIG. 9A, it is assumed that gas springs 704 have been compressed and locked in the compressed position and that cradles 702 have been pulled out into the extended position as shown. With cradles 702 in the extended position and gas springs 704 in the compressed position, a solution-filled syringe 900a-900c can be placed within channels 702a. As shown, the plunger of each syringe is in contact with end 704d of rod 704a.

FIG. 9A also shows that each syringe 900a-900c is coupled to input ports 710a-710c respectively while output port 710d is coupled to tubing that leads to the patient. Because the solution in syringe 900a (which is typically a medication) is intended to be injected first, syringe 900a is coupled to input port 710a. Syringe 900b, which typically includes saline that is intended to be injected second, is coupled to input port 710b. Syringe 900c, which typically includes heparin that is intended to be injected last, is coupled to input port 710c.

Once syringes 900a-900c are coupled to the appropriate input ports of sequencer 710 and loaded within syringe pumps 700a-700c, the sequenced infusion can be commenced. This can be accomplished by releasing locking structure 705 (e.g., by pulling up to remove locking pin 705a from notch 704a1 in rod 704a) on each housing 701 of syringe pumps 700a-700c. Preferably, this unlocking would be performed first on syringe pump 700a, then on syringe pump 700b, and finally on syringe pump 700c.

Figure 9B:
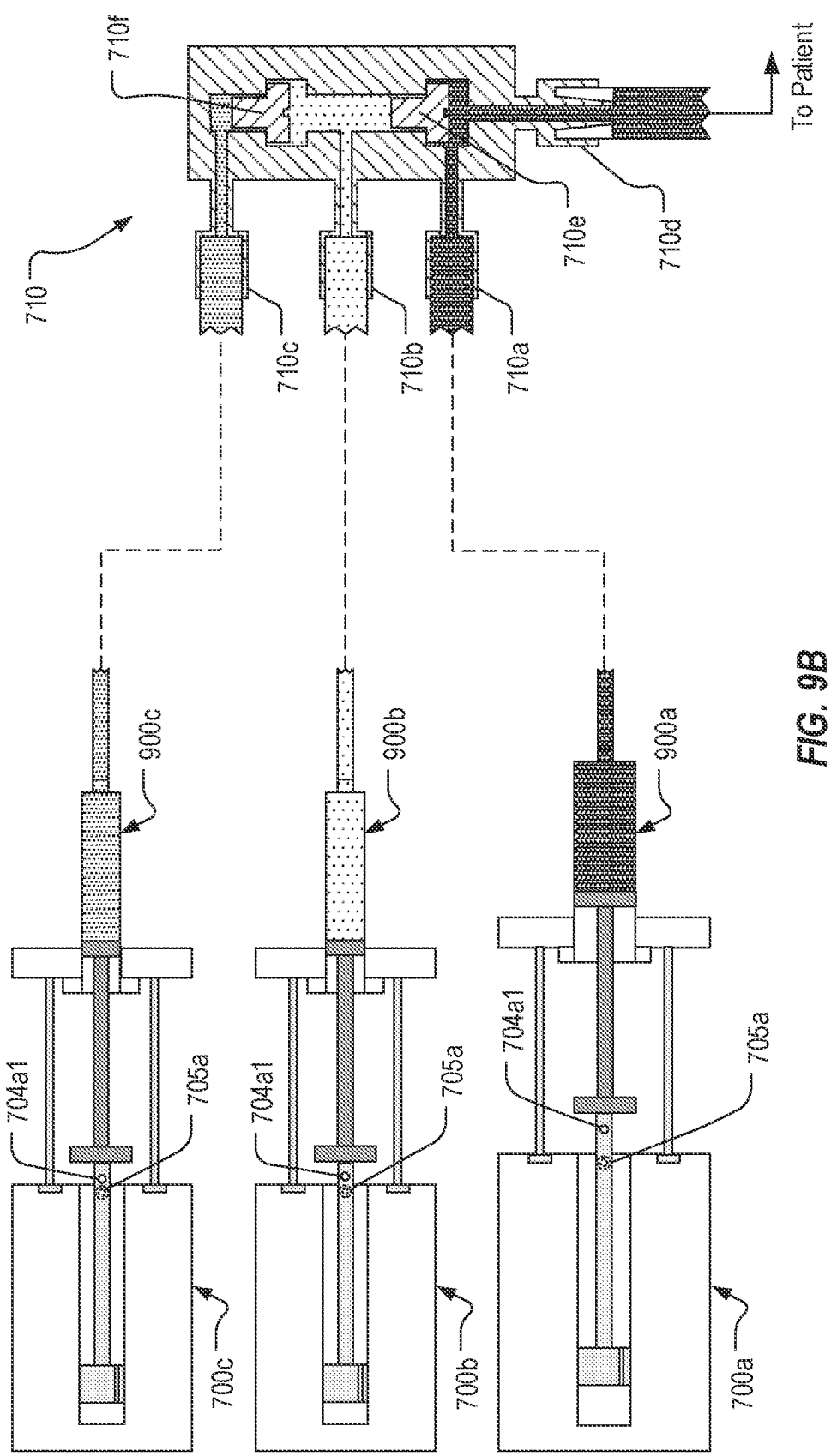

FIG. 9B illustrates the state of infusion pump 700 soon after locking structure 705 on each syringe pump 700a-700c has been released. As shown, the differential pressure on piston 704b is causing rod 704a to extend further towards the right. This movement in turn forces the plungers into syringes 900a-900c thereby injecting solution towards sequencer 710.

Because each gas spring 704 is designed to apply substantially the same force (and due to the tubing attached to output port 710d), the solution injected through each of input ports 710a-710c has substantially the same fluid pressure. This fluid pressure causes a similar force to be applied on poppets 710e and 710f. However, because the downstream side of each poppet has a larger frontal area than its upstream side, the fluid pressure applies a greater force on the downstream side. The net force on poppets 710e, 710f is therefore in an upstream direction (which would be towards the top of the page in FIG. 9B). This net force causes a seal to be formed between poppet 710e and the sidewall of lumen 800 thereby blocking the flow of solution. This net force will exist until syringe 900a empties. Accordingly, the solution from syringe 900a initially will flow through output port 710d while the solution from syringes 900b and 900c are blocked. It is noted that during this stage of the infusion, a similar net force is applied on poppet 710*f*.

Figure 9C:
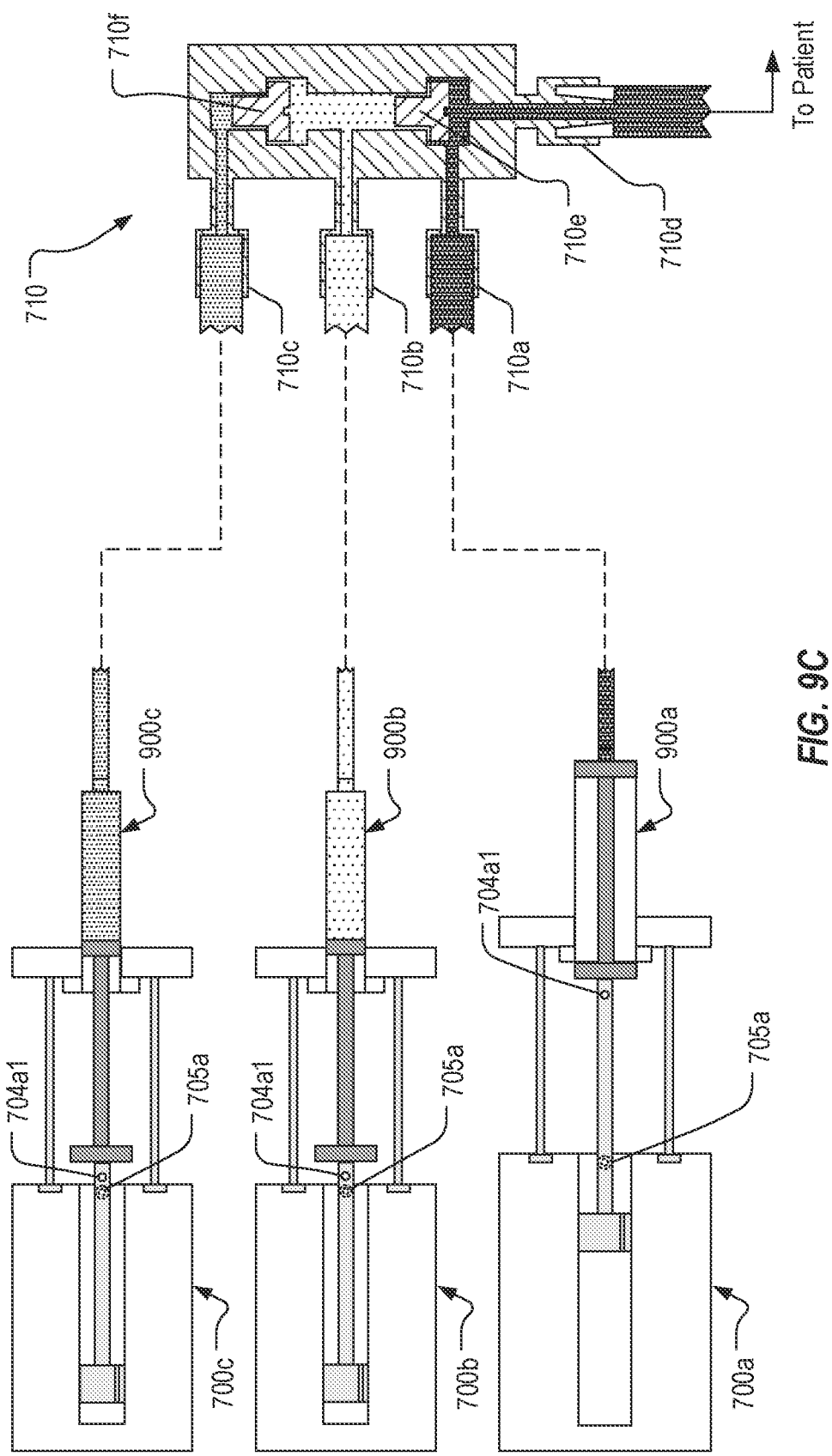

Because the solution from syringes 900*b* and 900*c* are blocked by poppets 710*e*, 710*f*, the extension of rod 704*a* within syringe pumps 700*b*, 700*c* will likewise be blocked (i.e., solution will not continue to flow out of syringes 900*b*, 900*c* while the solution within syringe 900*a* is being administered). Accordingly, as shown in FIG. 9C, rod 704*a* within syringe pump 700*a* is allowed to continue extending thereby injecting substantially all the solution from syringe 900*a*. Once the constant flow of solution from syringe 900*a* ceases (i.e., as syringe 900*a* empties), the force caused by the solution on the downstream side of poppet 710*e* will decrease to the point that it falls below the force applied to the upstream side of poppet 710*e*. Once this occurs, poppet 710*e* will move downstream such that solution from syringe 900*b* can commence flowing around poppet 710*e* and out through output port 710*d*. FIG. 9C represents the state of sequencer 710 as this transition is starting to occur. Accordingly, poppet 710*e* is shown as having moved slightly downstream. It is noted that this transition may occur while some solution from syringe 900*a* remains within the tubing as is shown.

At this point, absent the upstream force caused by the solution from syringe 900*a*, rod 704*a* of syringe pump 700*b* will commence extending thereby causing the solution from syringe 900*b* to be injected through sequencer 710. However, a net upstream force will remain applied to poppet 710*f* thereby preventing the solution from syringe 900*c* from flowing through sequencer 710.

Figure 9D:
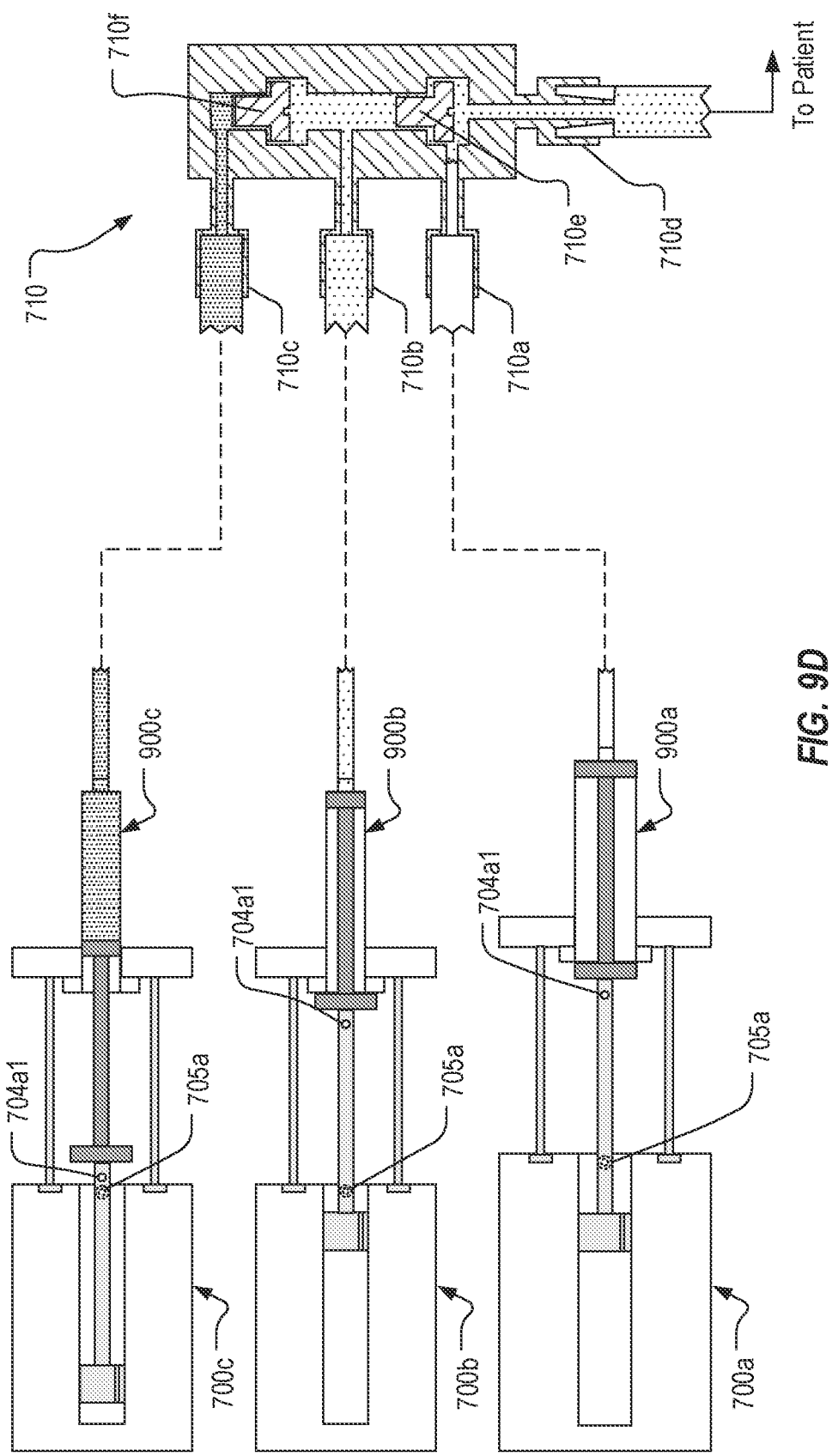
Figure 9E:
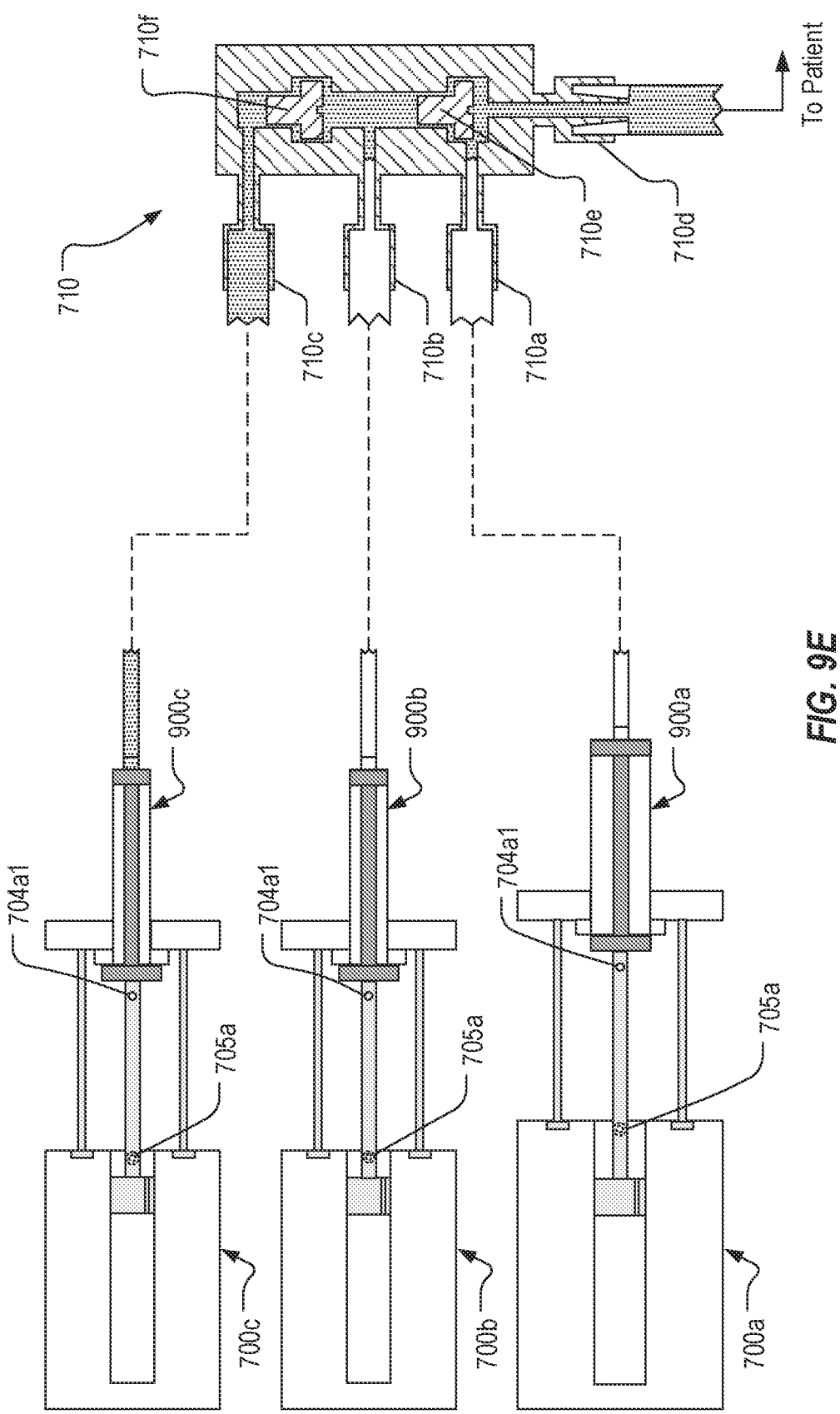
Figure 9F:
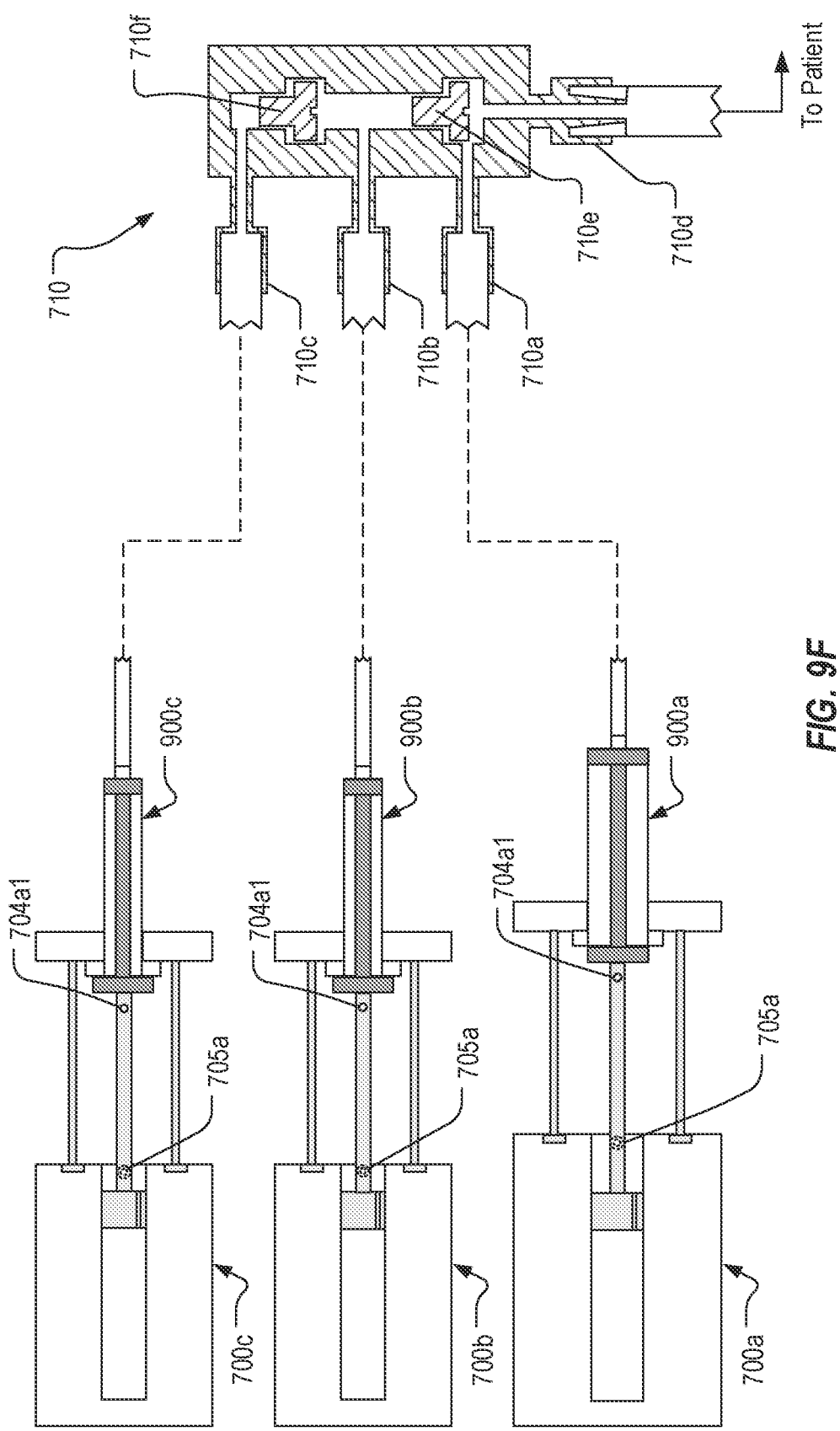

FIG. 9D represents the state of infusion pump 700 as the solution from syringe 900*b* is emptying. At this point, the upstream force on poppet 710*f* will begin to decrease allowing poppet 710*f* to move downstream as shown. Therefore, the solution in syringe 900*c* will begin to be injected as shown in FIG. 9E. Finally, syringe 900*c* will empty as shown in FIG. 9F.

Accordingly, the use of sequencer 710 facilitates the sequential administration of solutions from multiple syringes. The use of poppets to control this sequencing minimizes the design constraints on the syringe pumps. For example, because sequencer 710 provides sequencing without the need of differential fluid pressures, the syringe pumps can be more easily designed. In particular, due to the design of the poppets, a net upstream force can exist on the poppets even when the fluid pressures vary. For example, even if the solution from syringe 900*b* has a larger fluid pressure than the solution from syringe 900*a* (within acceptable limits), the differential frontal area will still cause a net upstream force on poppet 710*e*. For this reason, syringe pumps 700*a*-700*c* can be designed with less stringent requirements.

Figure 10A:
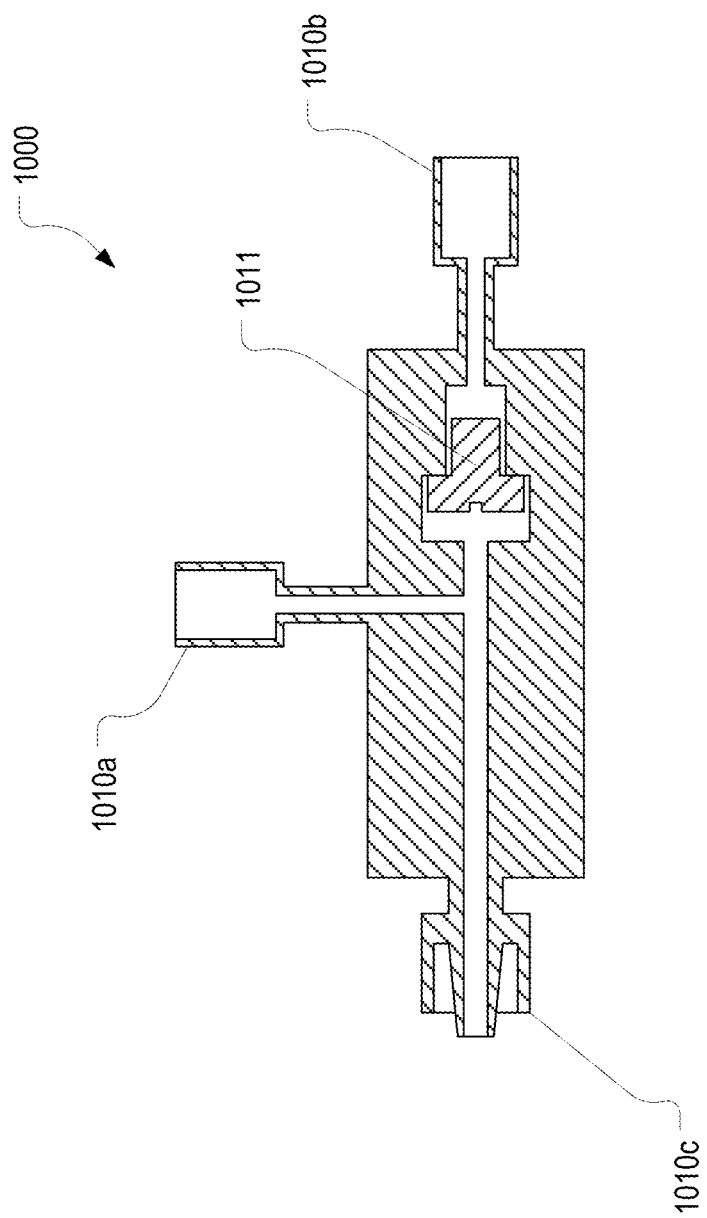
FIG. 10A illustrates an embodiment of a sequencer that is modular.
Figure 10B:
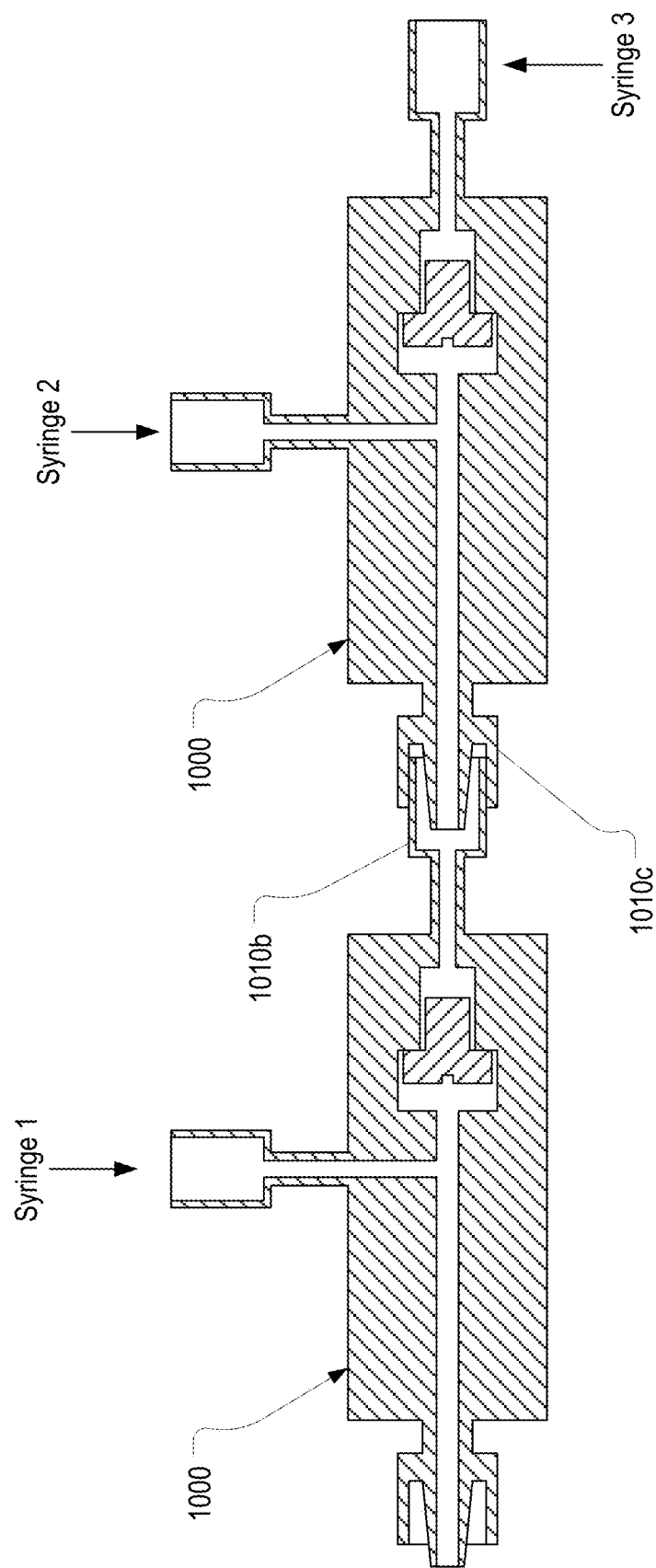
FIGS. 10B-10C each illustrates an example of how multiple sequencers of FIG. 10A can be combined in a modular fashion.
Figure 10C:
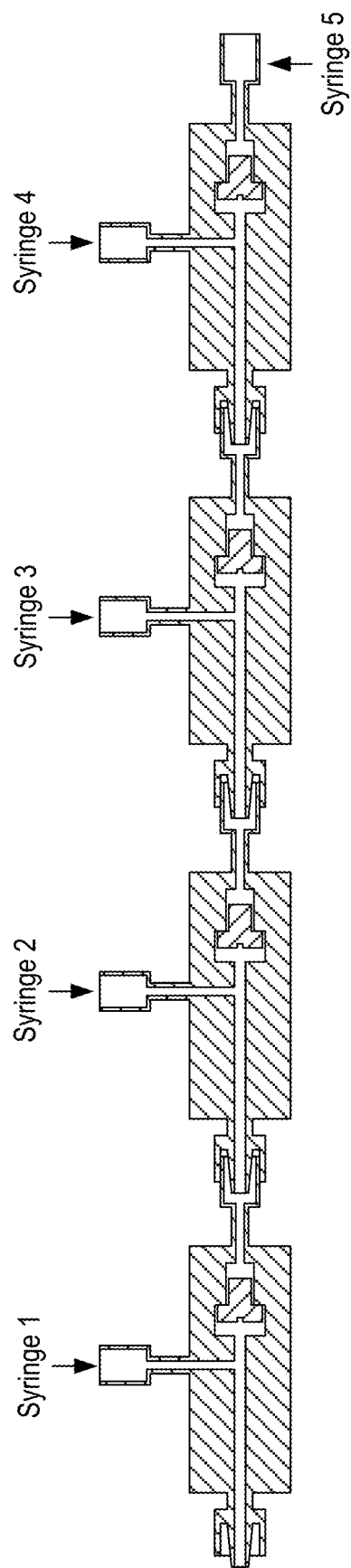

In some embodiments, a sequencer may be modular thereby allowing multiple sequencers to be interconnected. FIGS. 10A-10C illustrate an embodiment of a sequencer 1000 that is configured to be modular. Sequencer 1000 is similar to sequencer 710 in that it includes a poppet 1011 between each input port 1010*a*, 1010*b*. Poppet 1011 can be configured in the manner described above to cause solution injected through input port 1010*a* to be administered prior to solution injected through input port 1010*b*. Sequencer 1000 could be used alone to sequentially administer solutions from two syringes as described above.

Input port 1010*b* can be configured to receive an output port 1010*c* of another sequencer 1000 as shown in FIG. 10B. In this way, two sequencers 1000 can be coupled together to allow three solutions to be sequentially administered. As shown, the solution to be administered first could be coupled through input port 1010*a* of the downstream sequencer 1000, the solution to be administered second could be coupled through input port 1010*a* of the upstream sequencer 1000, and the solution to be administered third could be coupled through the input port 1010*b* of the upstream sequencer 1000. With the two sequencers 1000 coupled in this manner, the injection can occur in the manner described above.

FIG. 10C illustrates that any number of sequencers could be coupled together to allow for the sequential administration of practically any number of solutions. In the depicted example, four sequencers 1000 are coupled together to allow five solutions to be sequentially injected.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description.

What is claimed:

1. A set of one or more syringe pumps, each syringe pump comprising:
   a housing having a proximal end and a distal end;
   a cradle that is coupled to the distal end of the housing via two shafts, the cradle being configured to slide between a retracted position in which the cradle is proximate to the distal end of the housing and an extended position in which the cradle is spaced from the distal end of the housing; and
   a spring that is contained within the housing, the spring including a rod that extends outwardly through the distal end of the housing such that the two shafts are positioned on opposing sides of the rod, the spring being configured to travel between a proximal position in which the rod is retracted into the housing and a distal position in which the rod extends distally from the housing, the spring being biased towards the distal position;
   wherein the cradle is configured to receive a syringe loaded with a fluid when the cradle is in the extended position and the spring is in the proximal position, and wherein the biasing of the spring towards the distal position causes a distal end of the rod to apply a force against a plunger of the syringe as the rod travels to the distal position.

2. The set of one or more syringe pumps of claim 1, wherein the housing includes a locking structure that retains the spring in the proximal position.

3. The set of one or more syringe pumps of claim 2, wherein the locking structure includes a locking pin that interfaces with the rod to retain the spring in the proximal position.

4. The set of one or more syringe pumps of claim 3, wherein the locking pin inserts into a notch in the rod.

5. The set of one or more syringe pumps of claim 1, wherein the set includes a single syringe pump.

6. The set of one or more syringe pumps of claim 1, wherein the set includes more than one syringe pump.

7. The set of one or more syringe pumps of claim 1, wherein the spring is a gas spring that applies a constant force against the plunger of the syringe as the rod travels to the distal position.

8. The set of one or more syringe pumps of claim 1, wherein the cradle includes a channel that receives the loaded syringe.

9. A set of one or more syringe pumps, each syringe pump comprising:
   a housing having a proximal end and a distal end;
   a cradle that is coupled to the distal end of the housing, the cradle being configured to slide between a retracted position in which the cradle is proximate to the distal end of the housing and an extended position in which the cradle is spaced from the distal end of the housing; and
   a spring that is contained within the housing, the spring including a rod that extends outwardly through the distal end of the housing, the spring being configured to travel between a proximal position in which the rod is retracted into the housing and a distal position in which the rod extends distally from the housing, the spring being biased towards the distal position, wherein the housing includes a locking structure that interfaces with the rod to retain the spring in the proximal position;
   wherein the cradle is configured to receive a syringe loaded with a fluid when the cradle is in the extended position and the spring is in the proximal position, and wherein the biasing of the spring towards the distal position causes a distal end of the rod to apply a force against a plunger of the syringe as the rod travels to the distal position.

10. The set of one or more syringe pumps of claim 9, wherein the set includes more than one syringe pump.

11. The set of one or more syringe pumps of claim 9, wherein the locking structure includes a locking pin that interfaces with the rod to retain the spring in the proximal position.

12. The set of one or more syringe pumps of claim 11, wherein the locking pin inserts into a notch in the rod to retain the spring in the proximal position.

13. The set of one or more syringe pumps of claim 9, wherein the cradle is coupled to the distal end of the housing via one or more shafts.

14. The set of one or more syringe pumps of claim 13, wherein the one or more shafts are two shafts that are positioned on opposing sides of the rod.

15. The set of one or more syringe pumps of claim 9, wherein the spring is a gas spring that applies a constant force against the plunger of the syringe as the rod travels to the distal position.

16. The set of one or more syringe pumps of claim 9, wherein the cradle includes a channel that receives the loaded syringe.

17. A medical infusion pump comprising:
   a sequencer; and
   multiple syringe pumps, each syringe pump comprising:
   a housing having a proximal end and a distal end;
   a cradle that is coupled to the distal end of the housing, the cradle being configured to slide between a retracted position in which the cradle is proximate to the distal end of the housing and an extended position in which the cradle is spaced from the distal end of the housing; and
   a spring that is contained within the housing, the spring including a rod that extends outwardly through the distal end of the housing, the spring being configured to travel between a proximal position in which the rod is retracted into the housing and a distal position in which the rod extends distally from the housing, the spring being biased towards the distal position, wherein the housing includes a locking structure that interfaces with the rod to retain the spring in the proximal position;
   wherein the cradle is configured to receive a syringe loaded with a fluid when the cradle is in the extended position and the spring is in the proximal position, and wherein the biasing of the spring towards the distal position causes a distal end of the rod to apply a force against a plunger of the syringe as the rod travels to the distal position.

18. The medical infusion pump of claim 17, wherein the spring is a gas spring that applies a constant force against the plunger of the syringe as the rod travels to the distal position.

19. The medical infusion pump of claim 17, wherein the cradle is coupled to the distal end of the housing via two shafts that are positioned on opposing sides of the rod.

20. The medical infusion pump of claim 17, wherein the sequencer has multiple input ports to which the loaded syringes are coupled via tubing and an output port, each of the input ports and the output port being in fluid communication with a lumen, the sequencer further including a poppet positioned within the lumen between each adjacent pair of the input ports.

* * * * *